United States Patent
Holmes et al.

(10) Patent No.: US 11,545,241 B1
(45) Date of Patent: Jan. 3, 2023

(54) SYSTEMS AND METHODS FOR ANALYTE TESTING AND DATA MANAGEMENT

(71) Applicant: Labrador Diagnostics LLC, Wilmington, DE (US)

(72) Inventors: Elizabeth A. Holmes, Palo Alto, CA (US); Sunny Balwani, Palo Alto, CA (US); Daniel Young, San Francisco, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 946 days.

(21) Appl. No.: 14/480,405

(22) Filed: Sep. 8, 2014

Related U.S. Application Data

(60) Provisional application No. 61/875,033, filed on Sep. 7, 2013, provisional application No. 61/875,687, filed on Sep. 9, 2013.

(51) Int. Cl.
G06Q 50/22 (2018.01)
G16H 10/40 (2018.01)
G06Q 10/06 (2012.01)

(52) U.S. Cl.
CPC ....... *G16H 10/40* (2018.01); *G06Q 10/06311* (2013.01)

(58) Field of Classification Search
CPC .. G06Q 50/22; G06Q 50/24; G06Q 10/06311; B01L 7/52; B01L 2300/1827; B01L 2400/0487; G01N 2035/00158; G01N 21/645; G01N 21/6428; G01N 21/64; G01N 1/31; G01N 1/34; G01N 1/40; G01N 30/02; G01N 2030/324; G01N 15/0205; G01N 2015/0288; G01N 2015/0294; G01N 30/16; G01N 30/24; B01D 15/161; B01D 15/26; G16H 10/40
See application file for complete search history.

(56) References Cited

U.S. PATENT DOCUMENTS

| | | |
|---|---|---|
| 5,055,263 A | 10/1991 | Meltzer |
| 5,061,449 A | 10/1991 | Torti et al. |
| 5,072,382 A | 12/1991 | Kamentsky |
| 5,089,229 A | 2/1992 | Heidt et al. |
| 5,112,574 A | 5/1992 | Horton |
| 5,130,238 A | 7/1992 | Malek et al. |
| 5,171,534 A | 12/1992 | Smith et al. |
| 5,186,162 A | 2/1993 | Talish et al. |
| 5,230,864 A | 7/1993 | Columbus |
| 5,270,163 A | 12/1993 | Gold et al. |
| 5,270,184 A | 12/1993 | Walker et al. |
| 5,273,905 A | 12/1993 | Muller et al. |
| 5,281,395 A | 1/1994 | Markart et al. |
| 5,281,540 A | 1/1994 | Merkh et al. |
| 5,292,658 A | 3/1994 | Cormier et al. |
| 5,310,652 A | 5/1994 | Gelfand et al. |
| 5,311,426 A | 5/1994 | Donohue et al. |
| 5,320,808 A | 6/1994 | Holen et al. |
| 5,322,770 A | 6/1994 | Gelfand |

(Continued)

*Primary Examiner* — Maroun P Kanaan

(57) ABSTRACT

Systems, methods, and devices are provided for clinical laboratory testing using less than 1 mL of sample collected from a subject. Some embodiments collect between 1 mL and about 10 uL of sample from a subject. A method is also provided for analyte testing, wherein a mobile computing device may be used for laboratory test requests and for handling of the analyte testing process.

9 Claims, 18 Drawing Sheets

(56) References Cited

U.S. PATENT DOCUMENTS

| | | |
|---|---|---|
| 5,324,481 A | 6/1994 | Dunn et al. |
| 5,380,487 A | 1/1995 | Choperena et al. |
| 5,393,903 A | 2/1995 | Graetzel et al. |
| 5,399,491 A | 3/1995 | Kacian et al. |
| 5,411,876 A | 5/1995 | Bloch et al. |
| 5,416,879 A | 5/1995 | Liu |
| 5,418,155 A | 5/1995 | Cormier et al. |
| 5,443,790 A | 8/1995 | Coeurveille et al. |
| 5,455,008 A | 10/1995 | Earley et al. |
| 5,455,166 A | 10/1995 | Walker |
| 5,456,652 A | 10/1995 | Eberle |
| 5,460,778 A | 10/1995 | MacIndoe, Jr. |
| 5,463,228 A | 10/1995 | Krause |
| 5,475,096 A | 12/1995 | Gold et al. |
| 5,480,784 A | 1/1996 | Kacian et al. |
| 5,483,799 A | 1/1996 | Dalto |
| 5,507,410 A | 4/1996 | Clark et al. |
| 5,518,923 A | 5/1996 | Berndt et al. |
| 5,527,257 A | 6/1996 | Piramoon |
| 5,527,670 A | 6/1996 | Stanley |
| 5,530,101 A | 6/1996 | Queen et al. |
| 5,545,540 A | 8/1996 | Mian |
| 5,550,060 A | 8/1996 | Saunders et al. |
| 5,551,241 A | 9/1996 | Boeckel et al. |
| 5,578,269 A | 11/1996 | Yaremko et al. |
| 5,578,270 A | 11/1996 | Reichler et al. |
| 5,580,529 A | 12/1996 | Devaughn et al. |
| 5,585,089 A | 12/1996 | Queen et al. |
| 5,588,946 A | 12/1996 | Graham et al. |
| 5,602,647 A | 2/1997 | Xu et al. |
| 5,620,898 A | 4/1997 | Yaremko et al. |
| 5,628,890 A | 5/1997 | Carter et al. |
| 5,639,665 A | 6/1997 | Arai et al. |
| 5,670,375 A | 9/1997 | Seaton et al. |
| 5,683,888 A | 11/1997 | Campbell |
| 5,693,233 A | 12/1997 | Schembri |
| 5,693,761 A | 12/1997 | Queen et al. |
| 5,693,762 A | 12/1997 | Queen et al. |
| 5,741,411 A | 4/1998 | Yeung et al. |
| 5,741,668 A | 4/1998 | Ward et al. |
| 5,758,443 A | 6/1998 | Pedrazzini |
| 5,772,962 A | 6/1998 | Uchida et al. |
| 5,777,079 A | 7/1998 | Tsien et al. |
| 5,779,981 A | 7/1998 | Danssaert et al. |
| 5,804,387 A | 9/1998 | Cormack et al. |
| 5,807,523 A | 9/1998 | Watts et al. |
| 5,821,337 A | 10/1998 | Carter et al. |
| 5,844,686 A | 12/1998 | Treptow et al. |
| 5,846,492 A | 12/1998 | Jacobs et al. |
| 5,854,033 A | 12/1998 | Lizardi |
| 5,854,684 A | 12/1998 | Stabile et al. |
| 5,859,205 A | 1/1999 | Adair et al. |
| 5,874,304 A | 2/1999 | Zolotukhin et al. |
| 5,876,995 A | 3/1999 | Bryan |
| 5,879,628 A | 3/1999 | Ridgeway et al. |
| 5,896,297 A | 4/1999 | Valerino |
| 5,902,549 A | 5/1999 | Mimura et al. |
| 5,906,795 A | 5/1999 | Nakashima et al. |
| 5,915,284 A | 6/1999 | Meltzer et al. |
| 5,925,558 A | 7/1999 | Tsien et al. |
| 5,939,291 A | 8/1999 | Loewy et al. |
| 5,960,160 A | 9/1999 | Clark et al. |
| 5,961,451 A | 10/1999 | Reber et al. |
| 5,980,830 A | 11/1999 | Savage et al. |
| 5,993,417 A | 11/1999 | Yerfino et al. |
| 6,013,528 A | 1/2000 | Jacobs et al. |
| 6,030,582 A | 2/2000 | Levy |
| 6,033,850 A | 3/2000 | Purvis |
| 6,042,909 A | 3/2000 | Dunleavy et al. |
| 6,054,297 A | 4/2000 | Carter et al. |
| 6,056,661 A | 5/2000 | Schmidt |
| 6,060,022 A | 5/2000 | Pang et al. |
| 6,063,341 A | 5/2000 | Fassbind et al. |
| 6,074,616 A | 6/2000 | Buechler et al. |
| 6,091,490 A | 7/2000 | Stellman et al. |
| 6,114,122 A | 9/2000 | Besemer et al. |
| 6,115,545 A | 9/2000 | Mellquist |
| 6,116,067 A | 9/2000 | Myers et al. |
| 6,121,054 A | 9/2000 | Lebl |
| 6,136,535 A | 10/2000 | Lorincz et al. |
| 6,143,250 A | 11/2000 | Tajima |
| 8,158,430 B1 | 4/2012 | Roy et al. |
| 2005/0100937 A1 | 5/2005 | Holmes |
| 2007/0224084 A1 | 9/2007 | Holmes et al. |
| 2009/0088336 A1 | 4/2009 | Burd et al. |
| 2012/0029933 A1* | 2/2012 | Zubiller .......... G06F 19/328 705/2 |
| 2012/0309636 A1* | 12/2012 | Gibbons .......... B04B 5/0421 506/9 |
| 2013/0115685 A1 | 5/2013 | Holmes et al. |
| 2014/0170735 A1* | 6/2014 | Holmes .......... G01N 21/07 435/287.1 |
| 2015/0132860 A1* | 5/2015 | Cook .......... G01N 35/1079 436/501 |

* cited by examiner

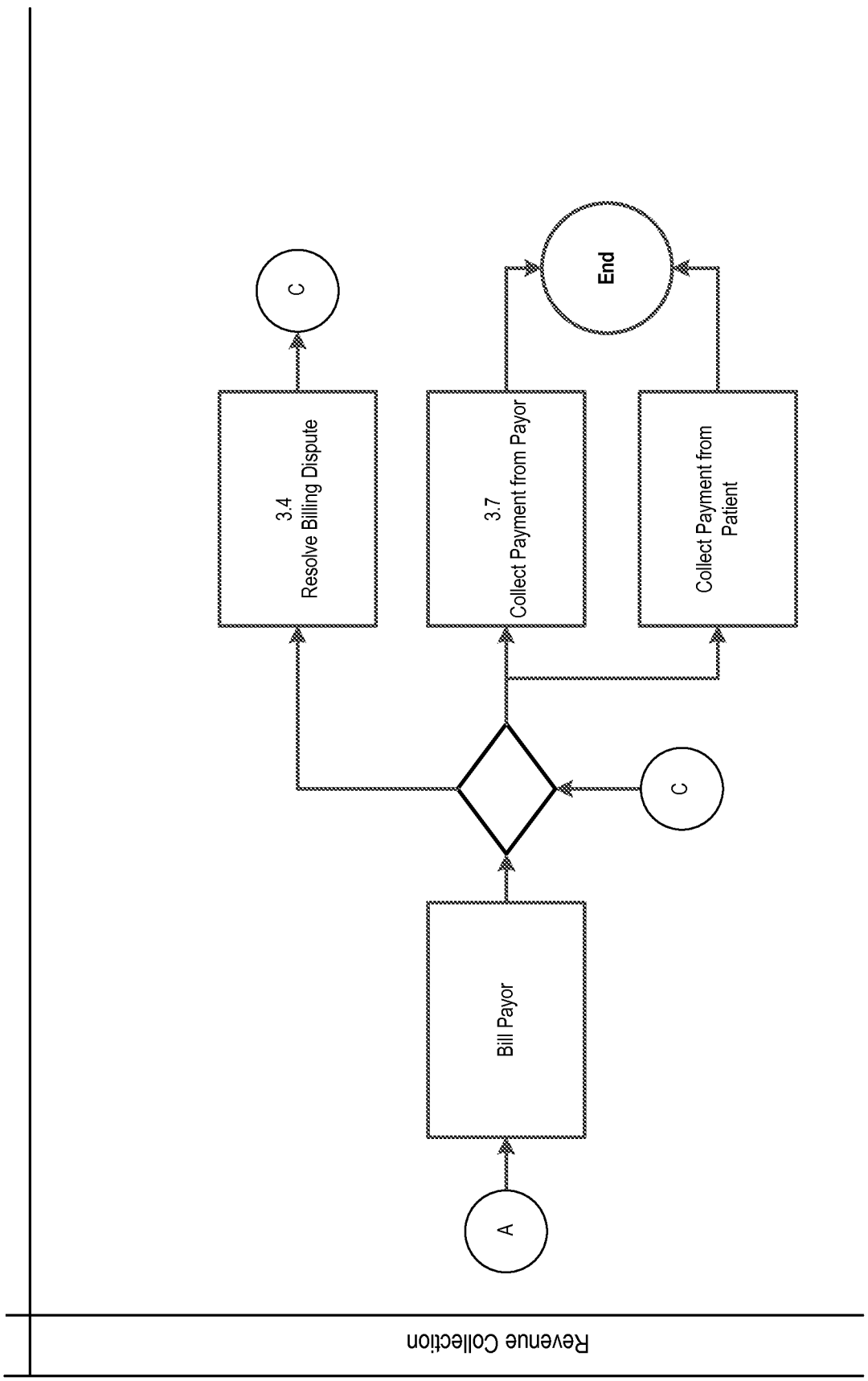
FIG. 3 CON'T

SYSTEMS AND METHODS FOR ANALYTE TESTING AND DATA MANAGEMENT

BACKGROUND

Laboratory testing of blood samples from patients has traditionally been based on a physical, paper laboratory test request that a patient receives from a doctor. That physical document is usually then taken by the patient to a technician or administrator at a laboratory facility or a patient service center. Typically, after waiting for their turn at that facility or center, a patient is then attended to by a phlebotomist who extracts blood from the patient by way of venipuncture. Before venipuncture, the phlebotomist selects the correct number and type of vacuum blood collection tubes for the desired number and/or types of tests set forth in the laboratory test request. The phlebotomist ensures that blood from the venipuncture fills the correct number and types of tubes. Unless the laboratory tests were ordered STAT or other expedited basis, the patient will wait days or weeks before being notified of the results of the laboratory test. Usually, the notification comes from the doctor or someone in the doctor's office, not from the laboratory that conducted the test.

This process of traditional paper-based testing protocol and traditional testing infrastructure, creates a legacy system that can be unnecessarily slow and burdened by various limitations.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-2014 Theranos, Inc.

SUMMARY

The disadvantages associated with the prior art are overcome by at least some of the embodiments of systems and methods provided herein.

In at least one non-limiting embodiment, a method is provided comprising clinical laboratory testing using less than 1 mL of sample from a subject. Optionally, a method is provided comprising clinical laboratory testing using less than 1 mL but more than 20 uL of sample from a subject.

In at least one non-limiting embodiment, a method is provided comprising using a mobile computing device to schedule an appointment time for a laboratory test; displaying a laboratory test menu on the mobile computing device, selecting one or more tests from said test menu, wherein the test menu is variable-based on geographic location; and using eligibility software on the analyzer device and/or on website wherein the information about the subject and/or subject's coverage can be confirmed before analyte testing is begun and cartridge and/or reagents are opened and/or used.

It should be understood that embodiments in this disclosure may be adapted to have one or more of the features described below. In one nonlimiting example, the test menu may be based on where sample will be collected and/or where sample analysis will be conducted. The available tests may be the same in multiple jurisdictions. Optionally, tests from different jurisdictions will have different sets of available tests.

In embodiments, non-transitory tangible computer readable media comprising machine-executable code for implementing methods provided herein may be provided as a stand-alone and transportable product (e.g. a DVD, flash drive, magnetic tape, or other form of removable/insertable computer-readable media), such that the program or software stored thereon can be loaded onto one or more different computers, servers, or other computing devices, in order to implement one or more methods provided herein (or elements thereof). In other embodiments, non-transitory tangible computer readable media comprising machine-executable code for implementing methods provided herein may be provided as part of a computing system involving multiple components (e.g. a server or personal computer). In embodiments, a user may interact with software on a server via a client application running on a user device, which is coupled to the server via a network. For example, the software may include a WWW-based interface to allow a remote user/client to access and view account-related information. In embodiments, software running on a server may provide certain features to a user (e.g. a WWW-based interface), while performing various processes/operations on the server.

In embodiments, provided herein is a laboratory test apparatus taking the form of a machine readable storage medium (e.g., hard disk, CD, or other medium) (or multiple media) which contains a set of software instructions for execution by a processor for performing methods provided herein.

In embodiments, methods provided herein may be implemented using hardware, software, or a combination thereof. In embodiments, software code may be implemented using one or more processors, which may be distributed between one or more computing devices.

One or more configurations provide various embodiments of user interfaces and/or workflows as described herein. Optionally, some configurations provide various embodiments of test result user interfaces and/or workflows as described herein. Optionally, some configurations provide various embodiments for anonymous testing user interfaces and/or workflows. Optionally, some configurations provide various embodiments for appointment creation user interfaces and/or workflows. Optionally, some configurations provide various embodiments for returning user appointment creation user interfaces and/or workflows. Optionally, some configurations provide various embodiments for appointment viewing and editing user interfaces and/or workflows. Optionally, some configurations provide various embodiments for multiple appointment creation user interfaces and/or workflows. Optionally, some configurations provide various embodiments for test reordering user interfaces and/or workflows. Optionally, some configurations provide various embodiments for appointment viewing and editing user interfaces and/or workflows. Optionally, some configurations provide various embodiments for editing user profile information. Optionally, some configurations provide various embodiments of user interfaces and/or workflows related to insurance information for the user. Optionally, some configurations provide various embodiments of user interfaces and/or workflows related to dependent information for the user. Optionally, some configurations provide various embodiments of user interfaces and/or workflows related to payment information for the user. Optionally, some configurations provide various embodiments for user interfaces and/or workflows related to changing a password or other security feature(s). Optionally, some configurations provide various embodiments for user interfaces and/or workflows related to privacy, terms of use, and/or other use policies. Optionally, some configurations provide various embodiments of user interfaces and/or workflows related to user login, account setup, password recovery, and/or logout. Optionally, some configurations provide various embodiments for user interfaces and/or workflows related to scanning of physical laboratory test forms into the system. Optionally, some configurations provide show at least one embodiment of user interfaces and/or workflows related to editing user profile(s). Optionally, some configurations provide show various embodiments of user interfaces and/or workflows related to insurance information for the user. Optionally, some configurations provide show various embodiments of user interfaces and/or workflows related to dependent information for the user. Optionally, some configurations provide show various embodiments for user interfaces and/or workflows related to emergency contact information. Optionally, some configurations provide various embodiments for user interfaces and/or workflows related to searching for specialists. Optionally, some configurations provide various embodiments of user interfaces and/or workflows related to payment information for the user. Optionally, some configurations provide various embodiments for user interfaces and/or workflows related to user health condition. Optionally, some configurations provide various embodiments of user interfaces and/or workflows related to adding preferred or user selected doctor information into a user account. Optionally, some configurations provide show various embodiments of user interfaces and/or workflows related to adding preferred or user selected patient service center or other sample collection location information into a user account. Optionally, some configurations provide various embodiments for user interfaces and/or workflows related to managing appointment expiration alert(s). Optionally, some configurations provide various embodiments for user interfaces and/or workflows related to changing a user's password. Optionally, some configurations provide various embodiments for user interfaces and/or workflows related to obtaining user feedback on one or more features of the system and/or service. Optionally, some configurations provide various embodiments for user interfaces and/or workflows related to policy and terms related to use. Optionally, some configurations provide various embodiments of user interfaces and/or workflows related to user login and/or setup. Optionally, some configurations provide various embodiments for user interfaces and/or workflows related to user login and/or unlock screens. Optionally, some configurations provide various embodiments of user interfaces and/or workflows related to existing lab orders, test order details, and/or specifics on certain tests. Optionally, some configurations provide various embodiments for user interfaces and/or workflows related to panel details. Optionally, some configurations provide various embodiments for user interfaces and/or workflows related to creating a new test order. Optionally, some configurations provide various embodiments for user interfaces and/or workflows related to user information, contact details, and/or doctor search functionality. Optionally, some configurations provide various embodiments for user interfaces and/or workflows related to workflows.

Optionally, some configurations provide a schematic of a system according to one embodiment described herein. Optionally, some configurations provide a schematic of a system according to one embodiment described herein.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DESCRIPTION OF THE SPECIFIC EMBODIMENTS

Figure 1:
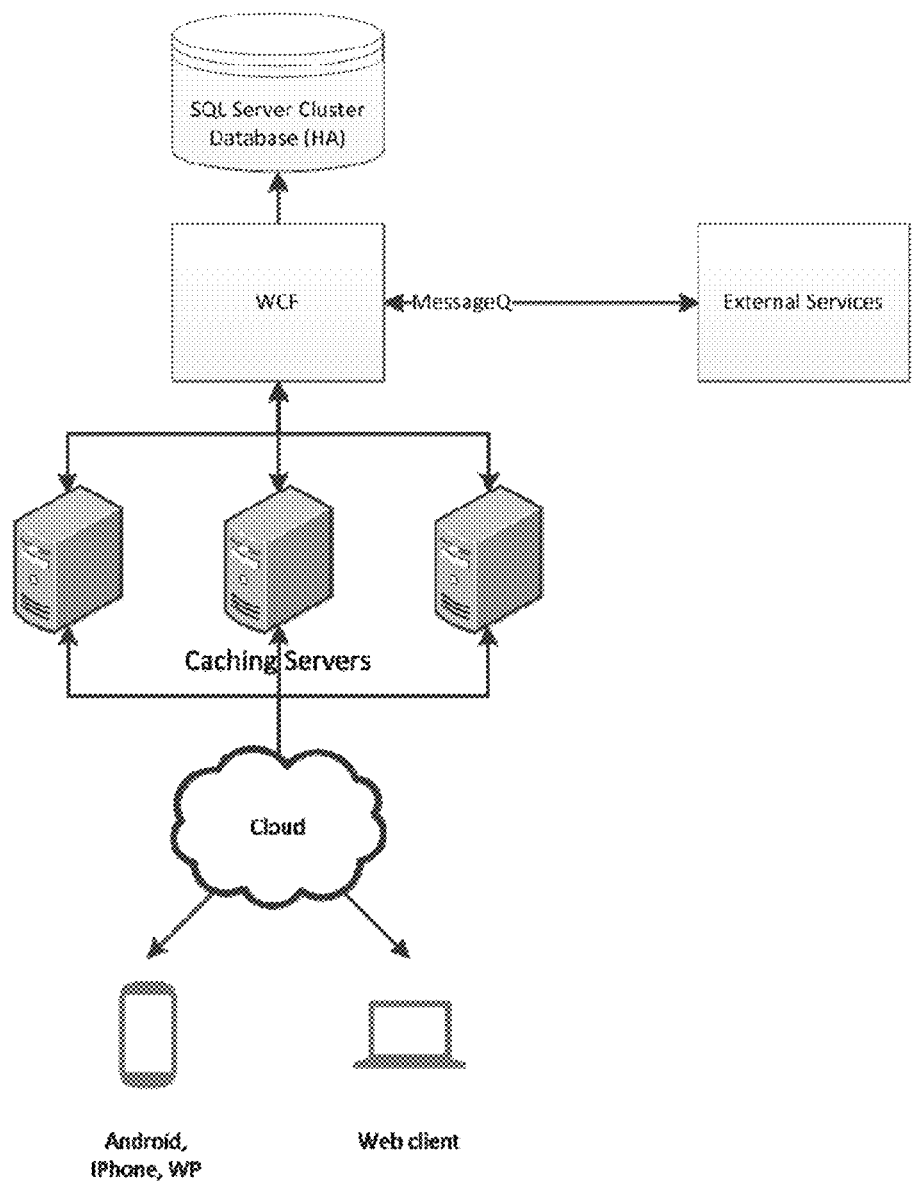
FIGS. 1 and 2 show schematics of various embodiments of systems as described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL. In some embodiments of the assays and methods disclosed herein, measurements may be made using a small volume blood sample, or no more than a small volume portion of a blood sample, where a small volume comprises no more than about 5 mL and at least 50 µL; or comprises no more than about 3 mL and at least 50 µL; or comprises no more than about 2 mL and at least 50 µL; or comprises no more than about 1 mL and at least 50 µL; or comprises no more than about 500 µL and at least 50 µL; or comprises no more than about 250 µL and at least 50 µL; or comprises no more than about 100 µL and at least 20 µL; or comprises no more than about 75 µL and at least 20 µL; or comprises no more than about 50 µL and at least 10 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

It should also be understood that for any and all of the user interface figures shown herein, a blue circle may be used to indicate where a user may tap, click, or otherwise select an object, item, or other feature visible on a user interface.

Figure 2:
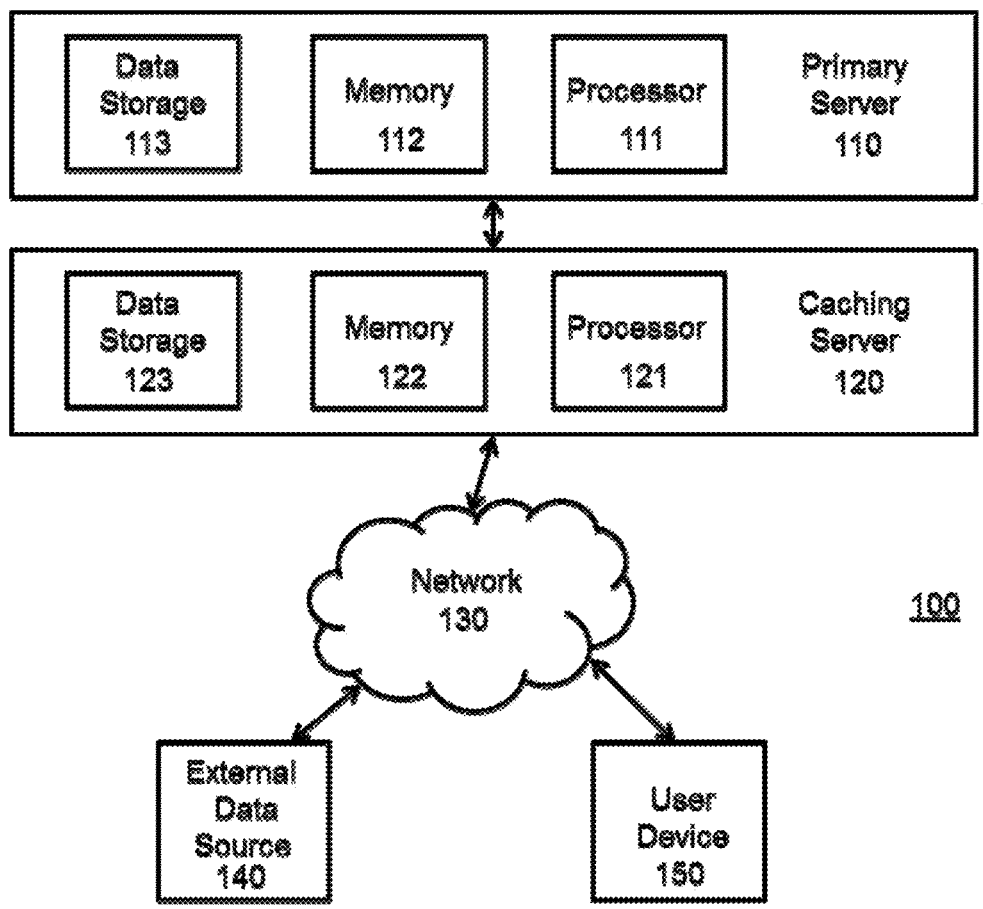
Figure 3:
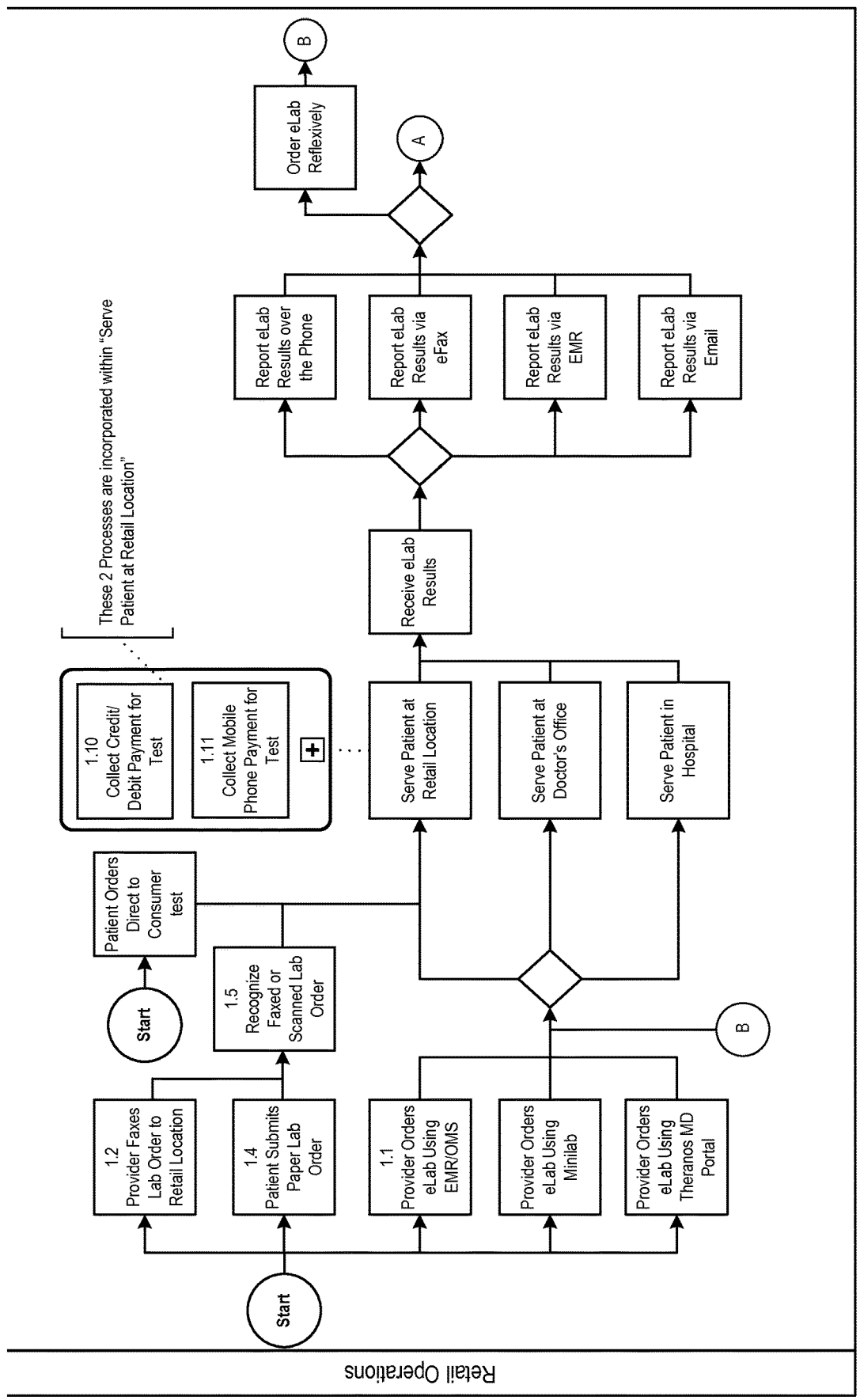
FIGS. 3 to 17 show schematics of various embodiments of methods and/or workflows as described herein.
Figure 4:
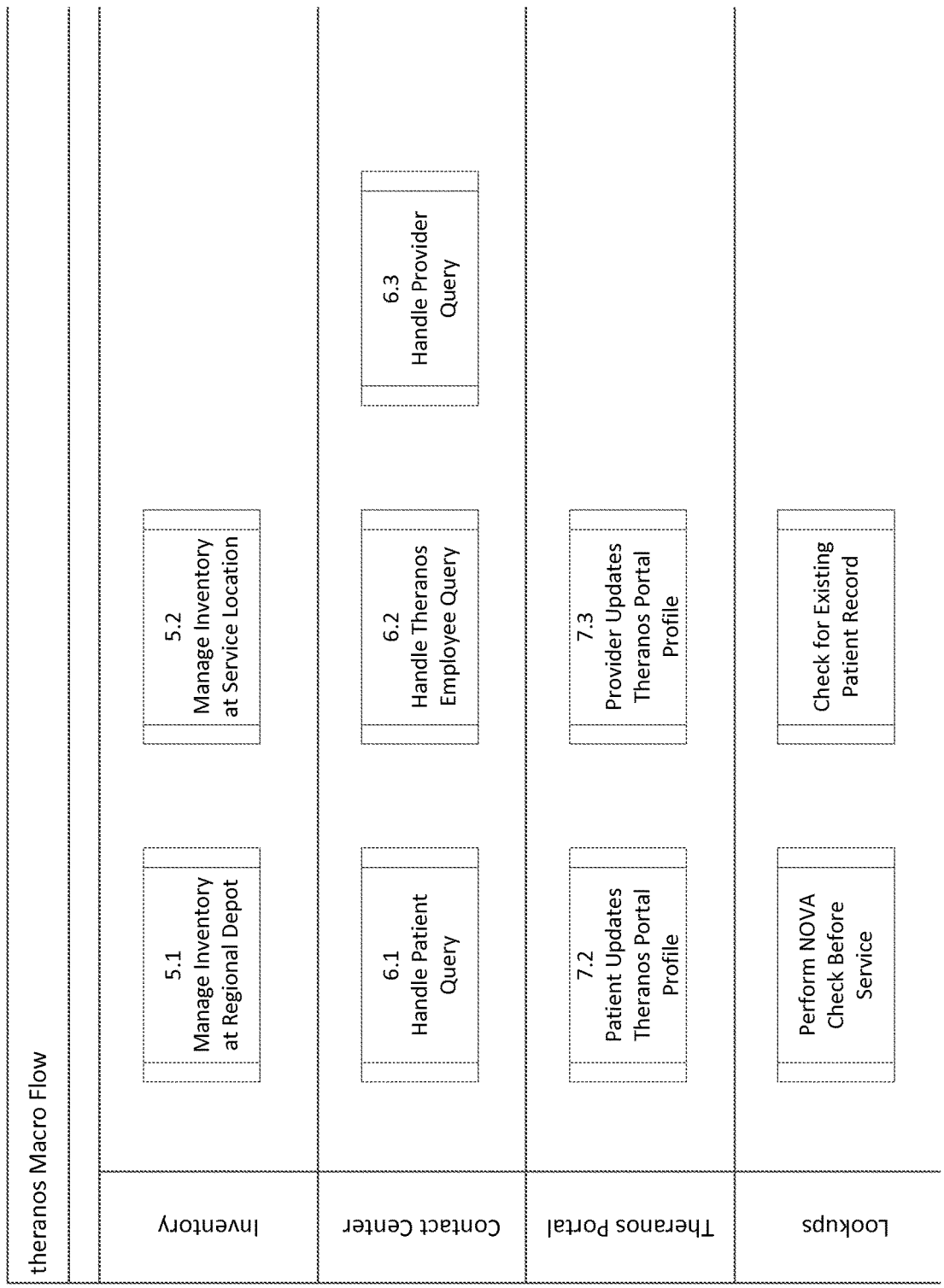
Figure 5:
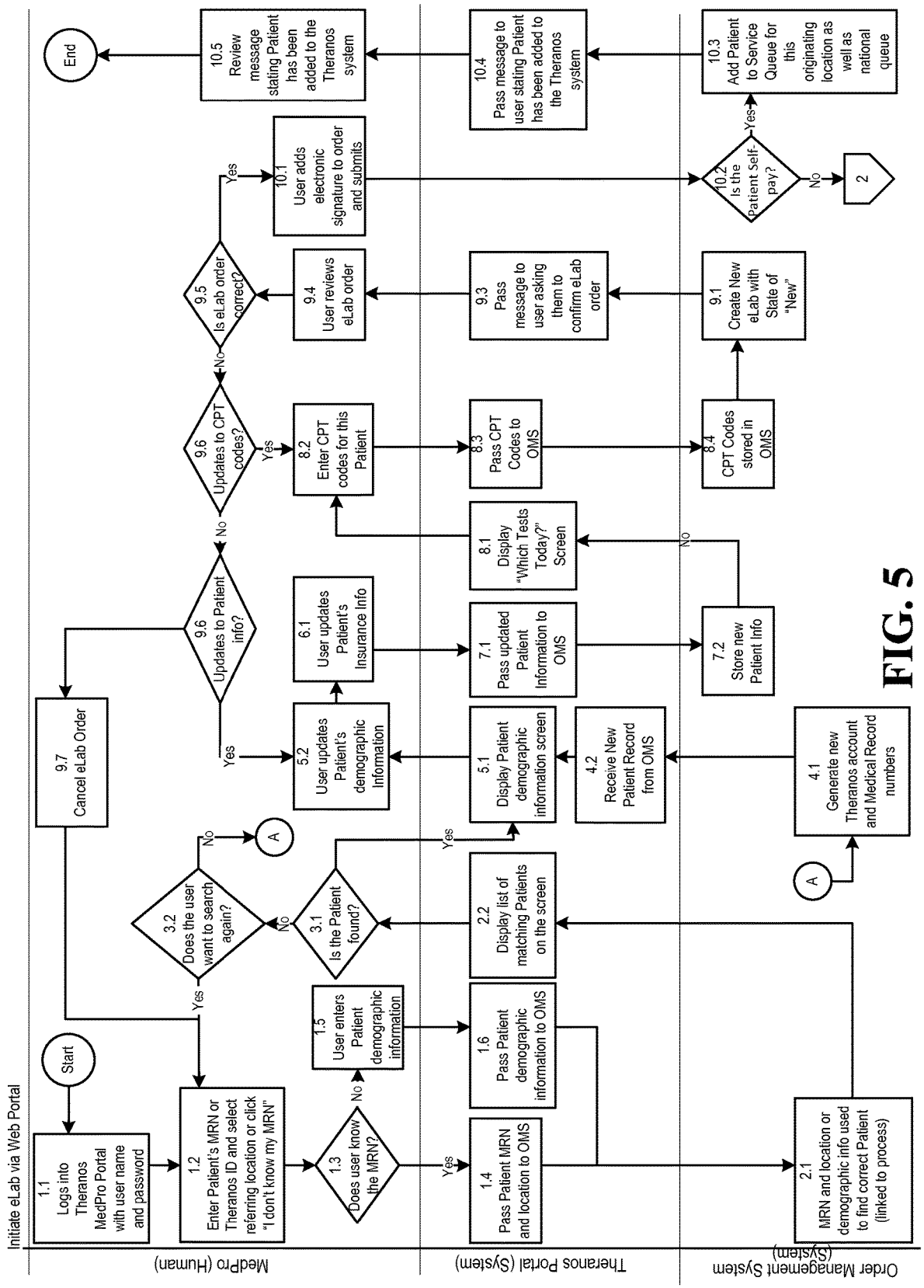
Figure 6:
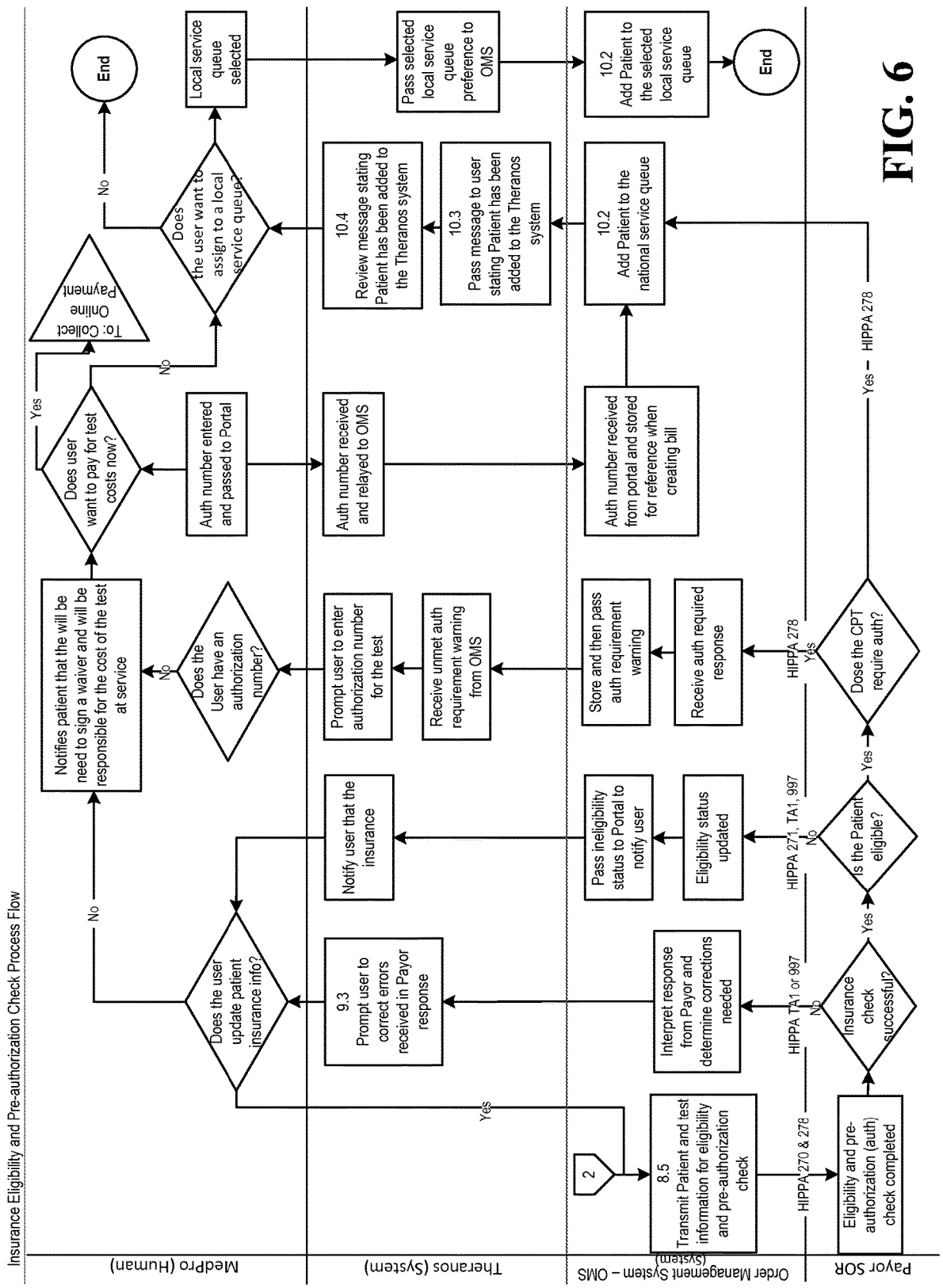
Figure 7:
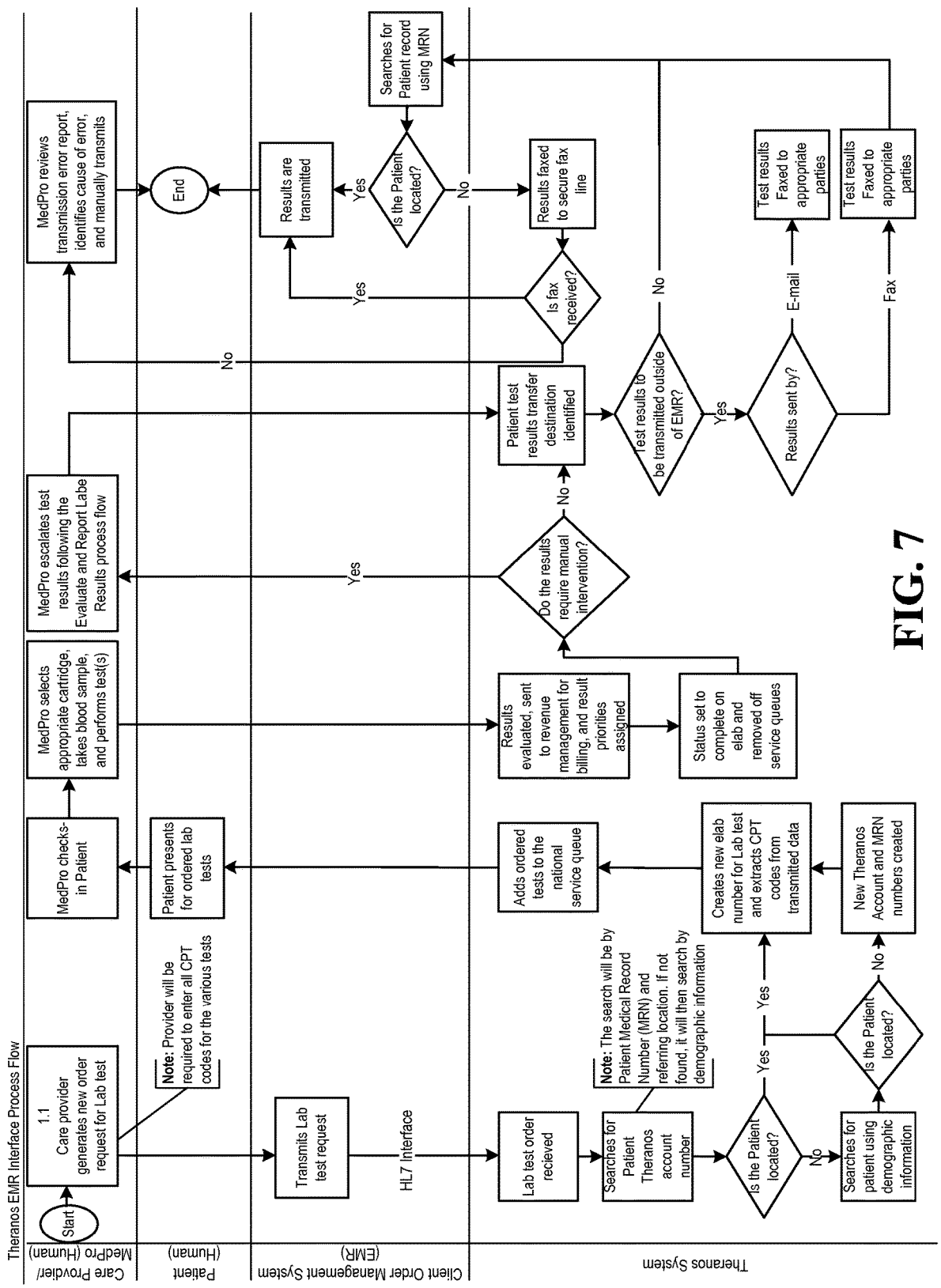
Figure 8:
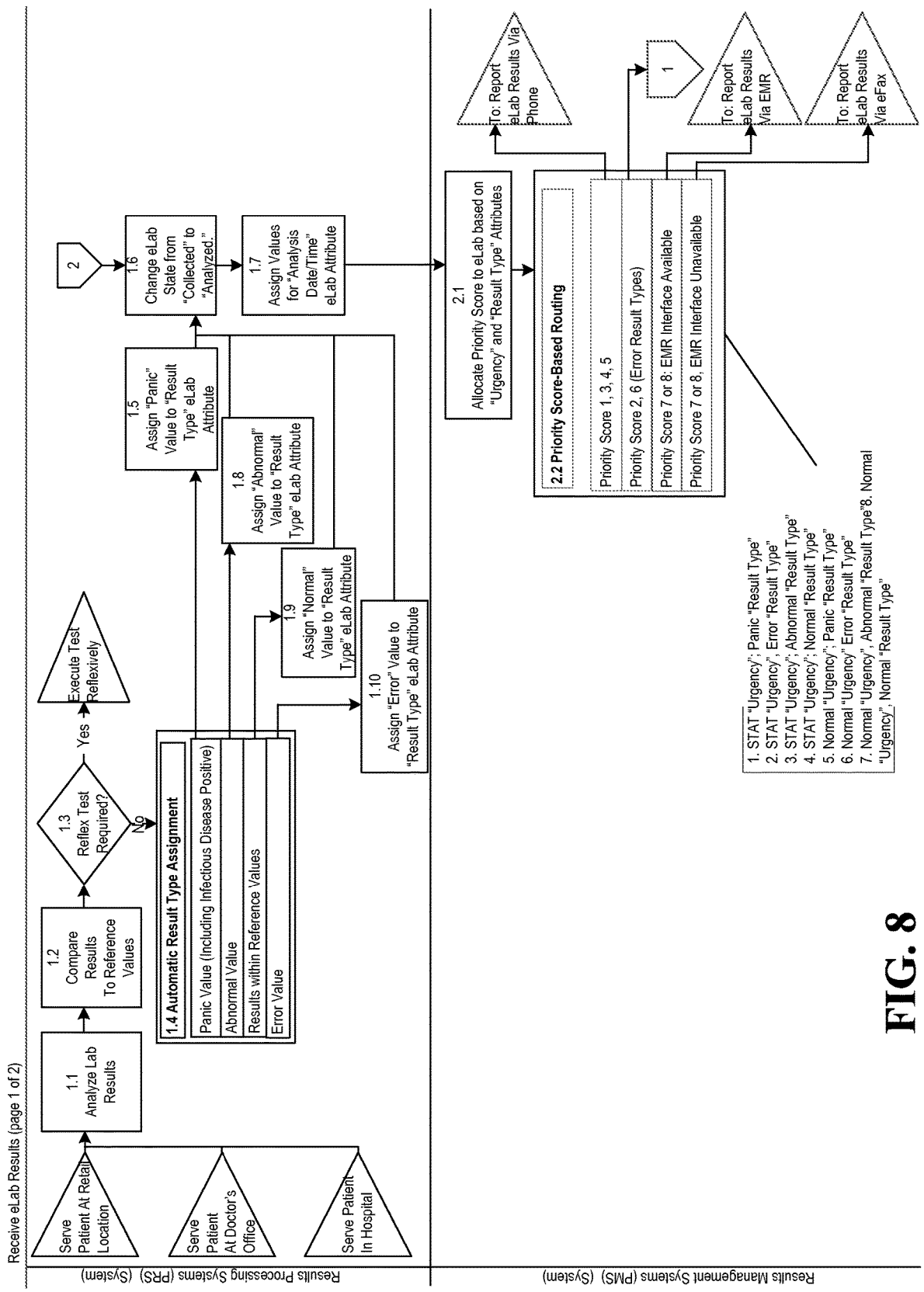
Figure 9:
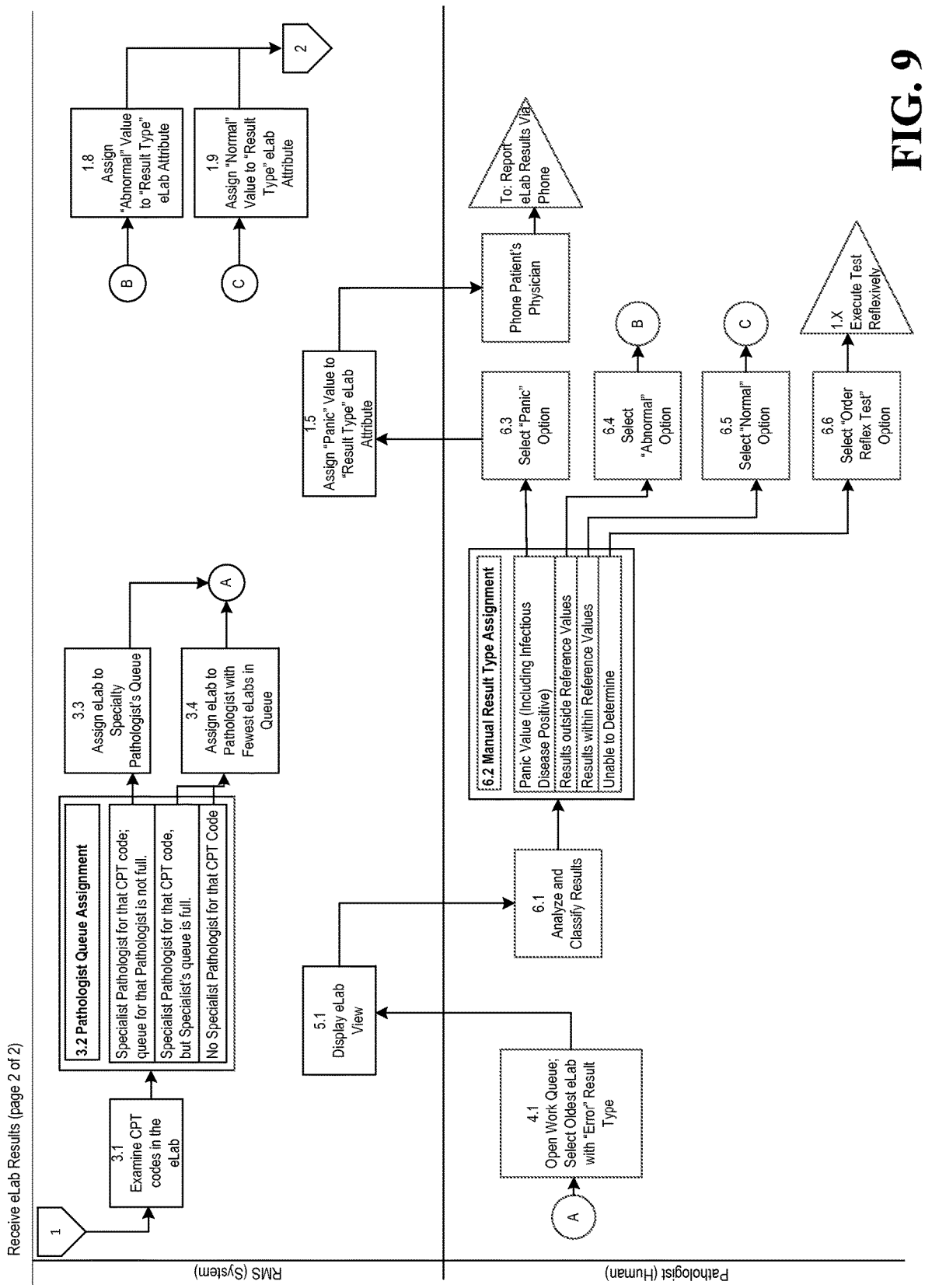
Figure 10:
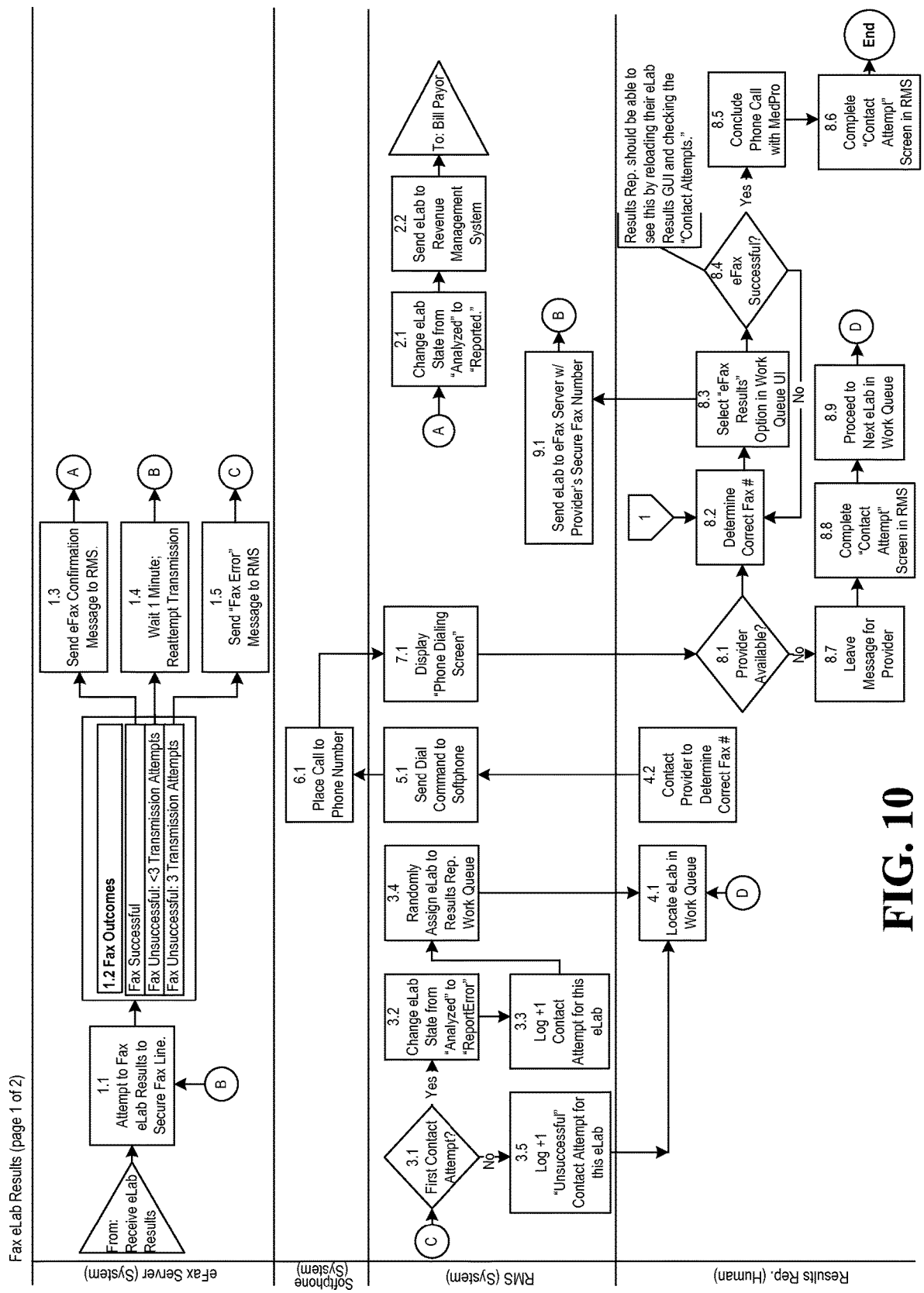
Figure 11:
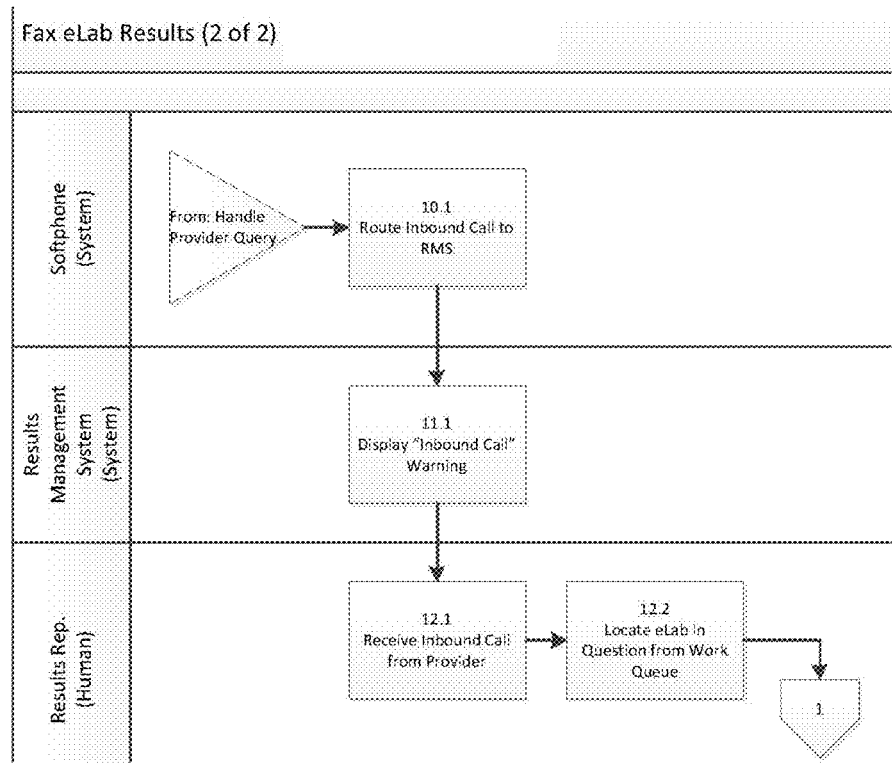
Figure 12:
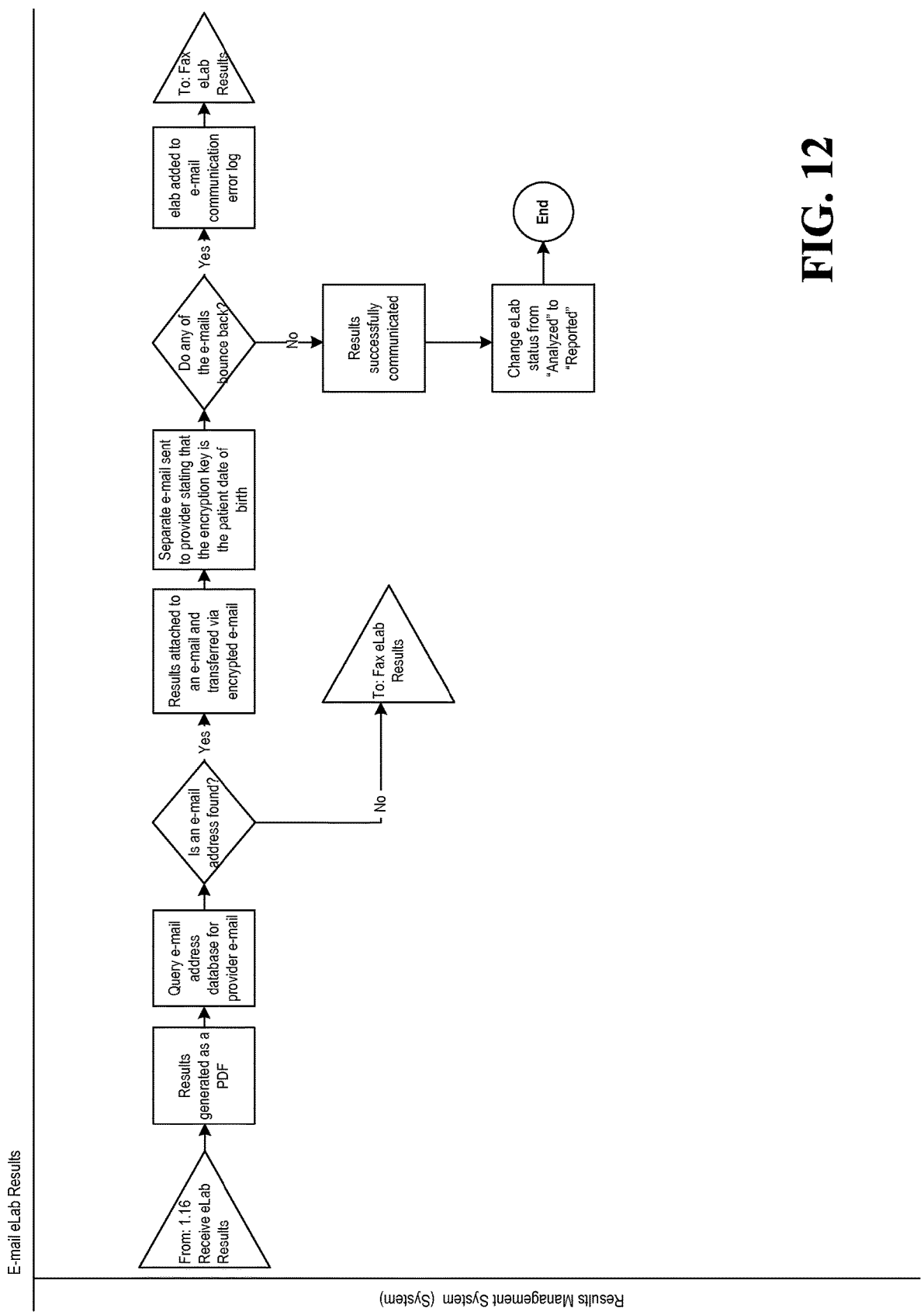
Figure 13:
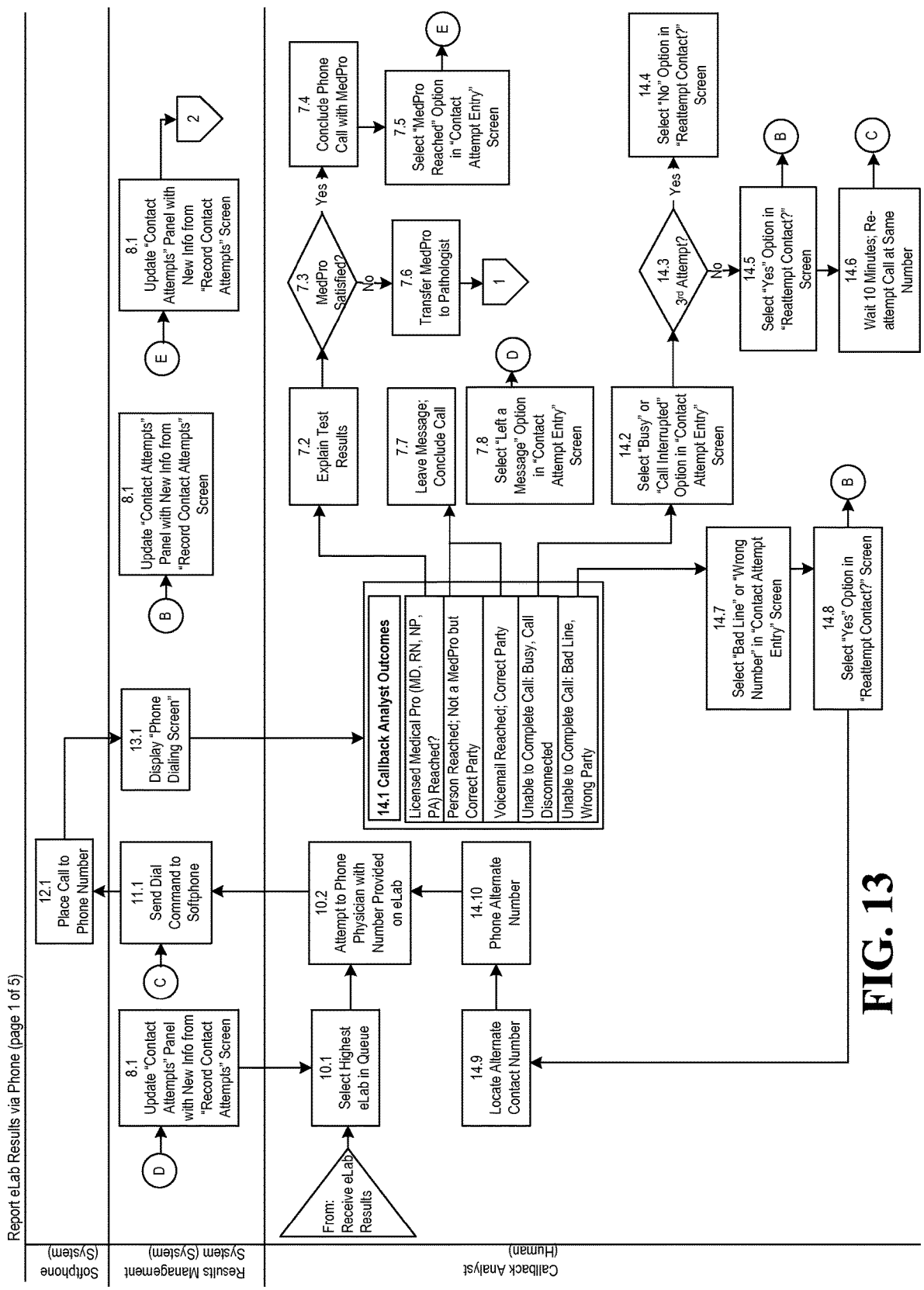
Figure 14:
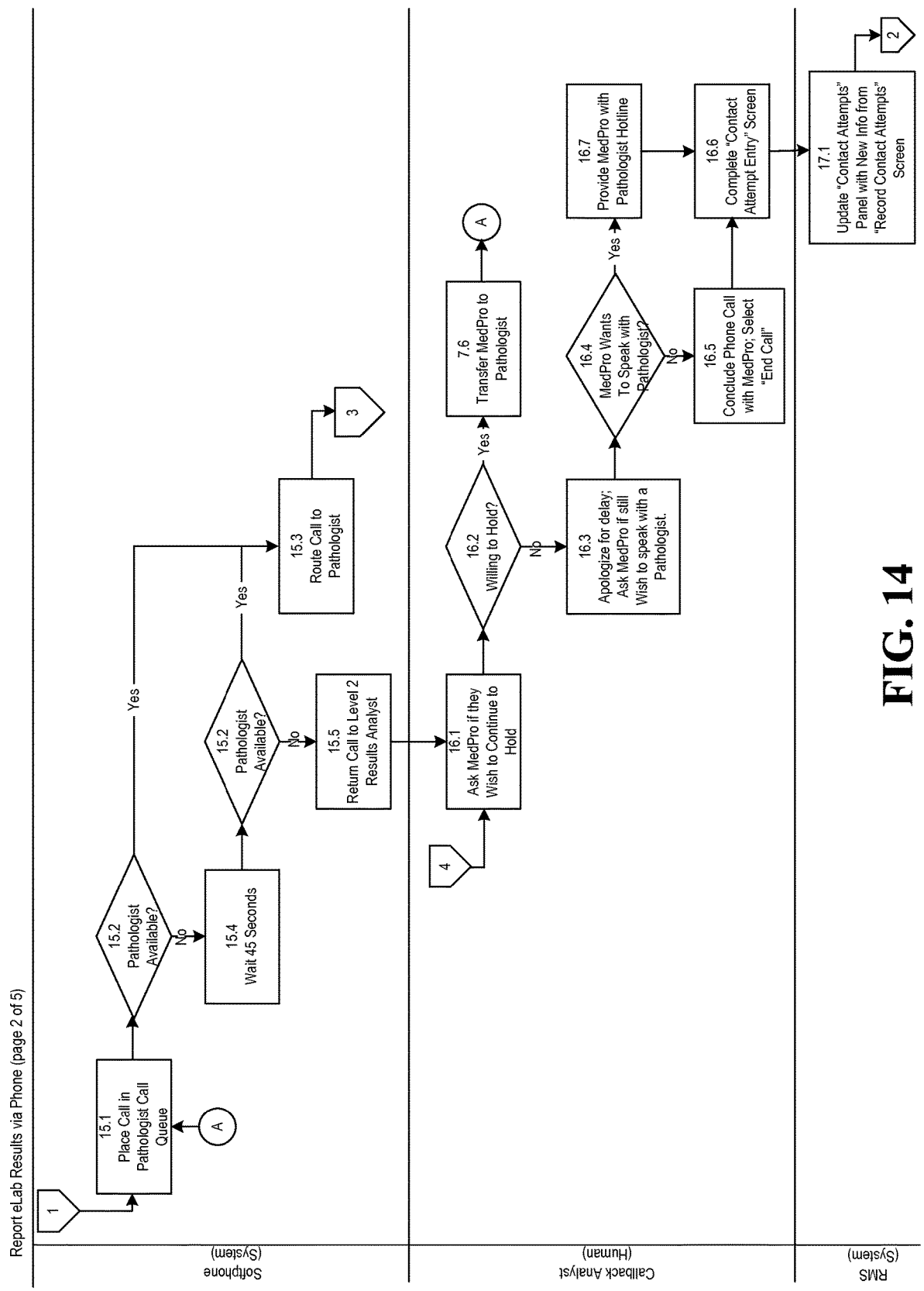
Figure 15:
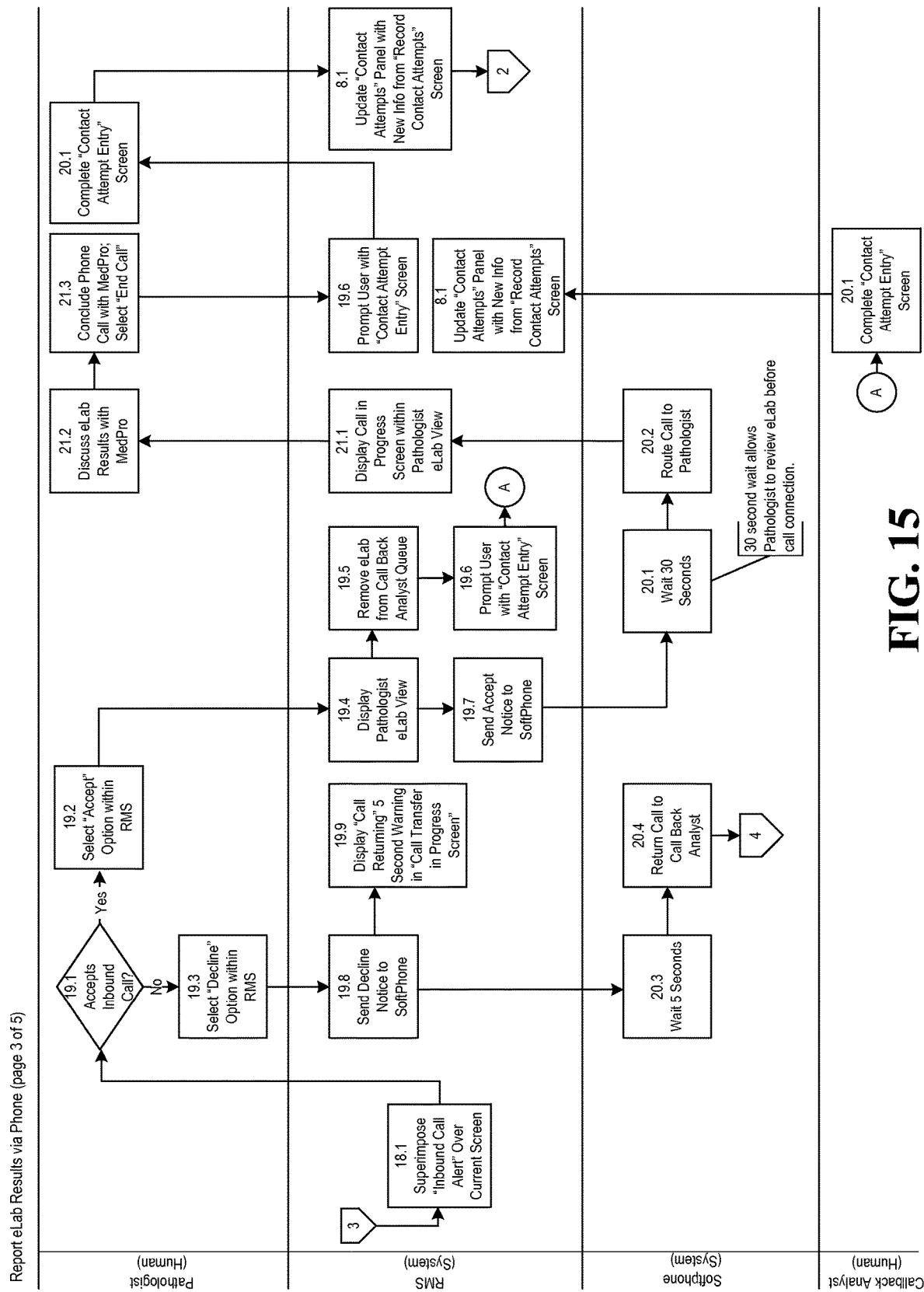
Figure 16:
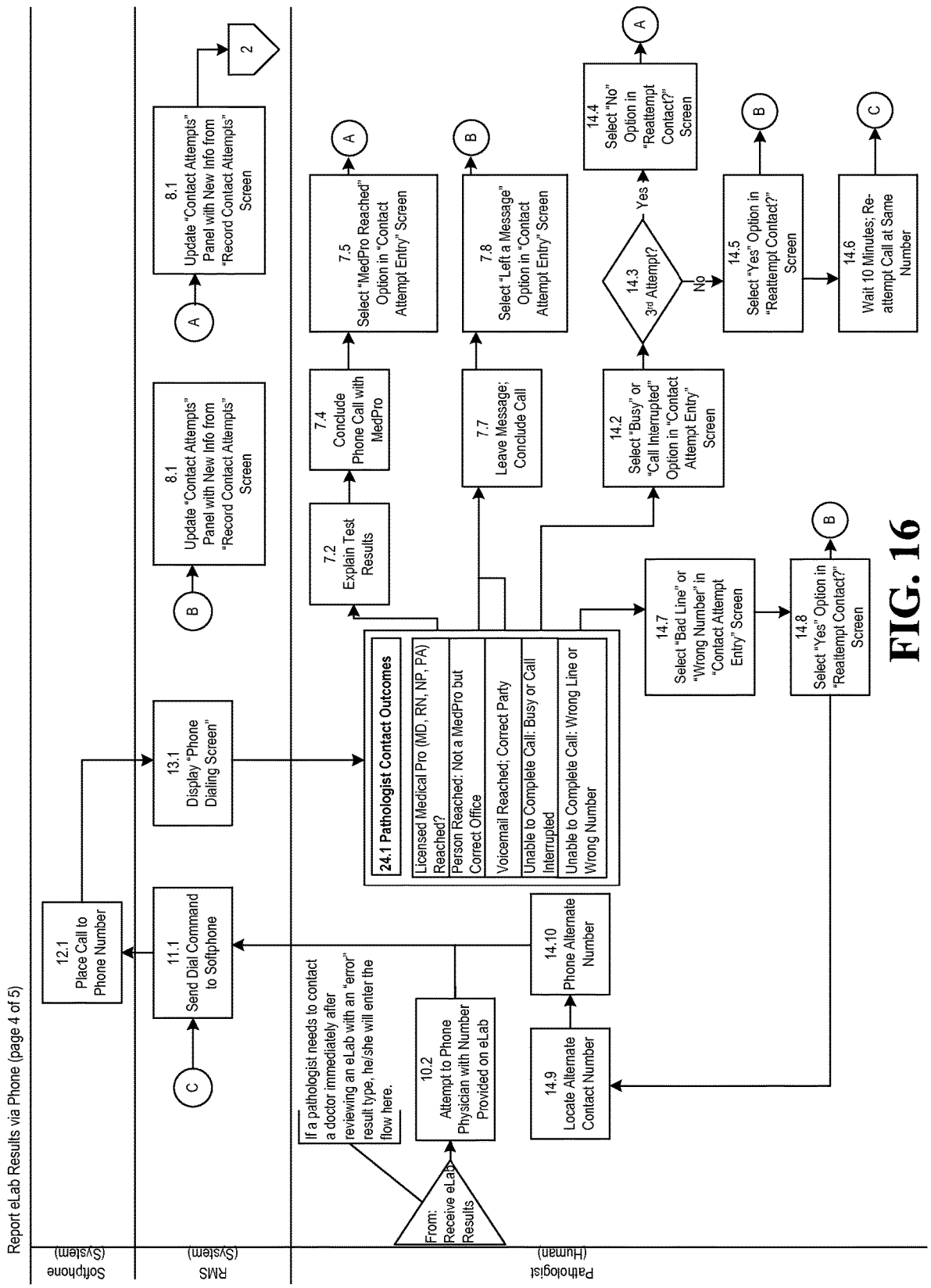
Figure 17:
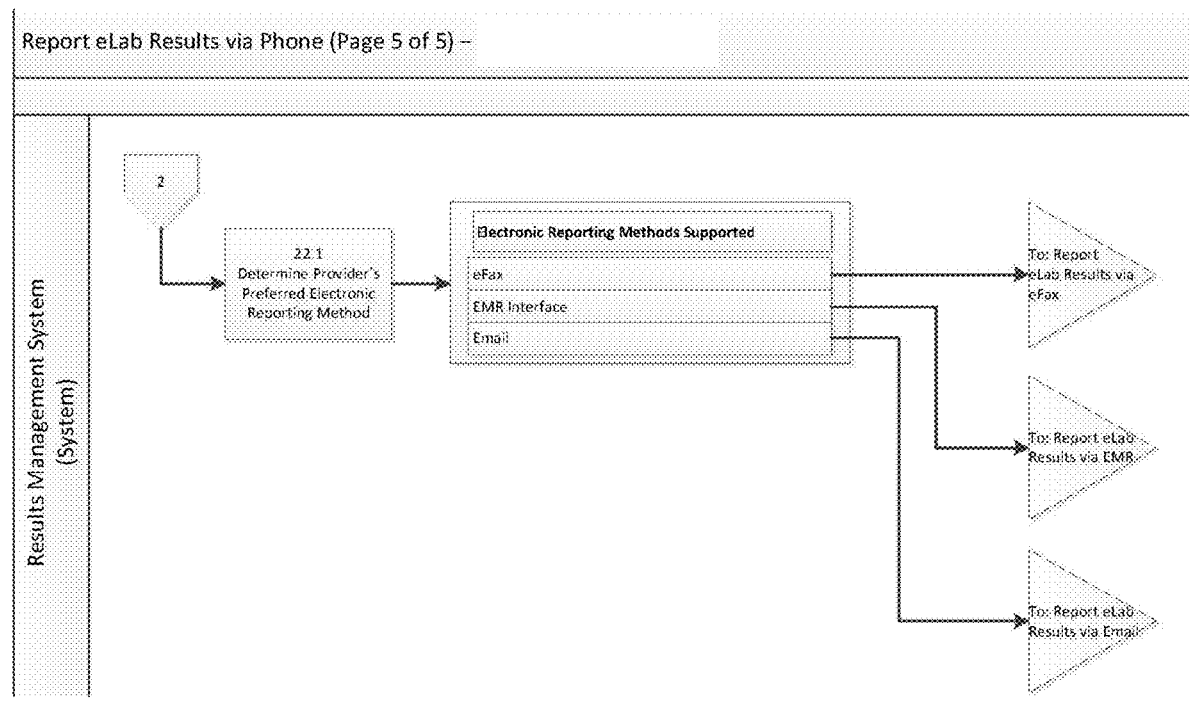

Referring now to FIGS. 1 and 2, exemplary embodiments of a system for use with the user interfaces, workflows, and/or other features is described herein. As seen in FIG. 1, there may be one or more caching servers that are in place to respond to data requests. In some embodiments, the caching server may not have the information requested. In such a scenario, the requesting device can already know to direct the request to the server with the data base, or optionally, for the caching server or other intermediary to direct the request to the server with the data. By way of example, the caching server can provide information that may be relevant to a geographic region or other factor for the server to be located in manner that responds the data request. Some embodiments may have scheduling information, location information, services information, or the like for users and/or locations in certain areas.

In one embodiment as seen in FIG. 2, the system 100 may involve, for example, a primary server 110, a caching server 120, a network 130, an external data source 140, and a user device 150. The primary server 110 may store or process data, such as laboratory test related information. The caching server 120 may also store or process data, although its major purpose may be to temporarily store copies of content which is also available in the primary server. The network 130 may be any structure which can support the operable connection of and data transfer between two or more computing devices, such as a local area network (LAN) or a wide area network (WAN), and may include, for example, an intranet or the Internet. The external data source 140 may be any computing device which may store, transmit, receive, or gather data that may be accessed by or sent to a server of the system. The user device 150 may be any computing device with which a user may review, input, or change laboratory test-related information. As used herein, a "computing device" refers to any device which may store, transmit, receive, gather, or process digital data, and may include, for example, servers, personal computers, data storage units, hard drives, portable digital media, smartphones, computer systems, mobile devices, external data sources, user devices, and websites. In embodiments, systems or elements thereof described herein may be implemented as a cloud-computing system.

A primary server 110 may contain, for example, a processor 111, a memory unit 112, and a data storage unit 113. The processor 111 of a server may be a hardware structure which performs computational operations of a computer program. In embodiments, a processor 111 may carry out instructions stored in a tangible computer readable medium. The processor 111 may contain one or more microprocessors. A memory unit 112 is a structure for storage of digital information which typically uses volatile storage and is rapidly or directly accessible by a processor (e.g. random access memory (RAM)). A data storage unit 113 is a structure for storage of digital information which typically uses non-volatile storage, and which typically has a much larger storage capacity than a memory unit 112, but is less quickly accessible by the processor 111 than the memory unit (e.g. hard drive). In embodiments, the memory unit 112 or data storage unit 113 may store non-transitory computer readable media, which may include, for example, code, logic, or instructions for performing methods provided herein. A primary server 110 may have any number of processors 111, memory units, 112, or data storage units 113 (e.g. 1, 2, 3, 4, 5, 6, 7, 8, 9, 10, 15, 20, 25, 50, 100, 1000, or more of any or each of the processors, memory units, or data storage units). A primary server 110 may also contain other components, such as a removable media drive (which may accept, for example, CDs, DVDs, floppy disks, or magnetic tape-based storage), input-output (I/O) channels, buses, network interfaces (wired or wireless structures for facilitating data transfer between a server a network), or power supplies. A primary server 110 may have a variety of different shapes and structures. For example, a primary server 110 may be a dedicated server, or it may be part of a computer which contains other features (e.g. a monitor, peripherals, etc.). In some embodiments, the primary server 110 may be part of, for example, a personal computer or a smart phone.

Optionally, a system provided herein may contain non-transitory tangible computer readable media. Computer readable media can be any available media which can be directly or indirectly accessed by a processor or server of a system provided herein. Computer readable media may include volatile and nonvolatile media, as well as removable and non-removable media. Computer readable media may be implemented in any method or technology for storage of information, such as computer readable instructions, data structures, program modules, or other data. Computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage device, or any other medium which can be used to store information and which may be accessed by a processor or server.

Optionally, a server may be operably connected to one or more external data source 140 (e.g. a website with information of interest, a GPS associated with a computing device of interest, a different server, a hard drive); the server may obtain information from such sources as-needed or at regular intervals. In embodiments, a server may include data mining hardware or software, such as software configured to search the Internet or predetermined web sites (e.g., "weather.com") on the internet to obtain data of interest. In embodiments, an external data source 140 may be a data storage unit operably connected to the server. A server may have load balancing, task management, and backup capacities. The components of a server may be within a single housing unit, or they may be distributed between two or more housing units. A server may be implemented as a distributed network of processors, memory, and storage units. A server may contain or be operably connected to a database (for example, the database may be in a data storage unit of the server or in an external data source). The processor of a server may run a computer program or software, the instructions of which may be provided from, for example, a data storage unit, removable media, or a data storage unit operably connected to the server. In embodiments, two or more servers may act together to function as a server. Servers may communicate with any number and type of computing devices. The server may engage in one-way or two-way communication with computing devices. Other server components or configurations not explicitly discussed herein but known in the art may be included in servers and systems described herein.

By way of non-limiting example, the primary server 110 may contain or be operably connected one or more databases of information relevant to laboratory testing. For example, databases may contain information relating to users or patient accounts, such as patient home addresses, patient contact information (e.g. phone number, e-mail address), billing information, emergency contact information, insurance information, appointment histories, medical records, user login names and passwords, patient healthcare provider information, or other information. The primary server 110 may, with the aid of a processor, use data from one or more sources to perform methods relating to laboratory test analysis or scheduling Optionally, the caching server 120 may have any of the components or configurations of the primary server 110 described elsewhere herein. Generally, the caching server 120 is optimized for temporary storage of frequently-accessed content from the primary server 110, in order to increase the speed at which the content can be delivered to a client/user and to decrease the number of operations required to be performed by the primary server 110 (and in turn, to increase the performance of the primary server 110). The caching server 120 may store content in either or both of the memory unit 122 or data storage unit 123. In systems and methods provided herein, the caching server may store, for example, appointment information for one or more health service centers. The caching server 120 may be configured to regularly update from the primary server 110 its cached content. In embodiments, a caching server 120 may be located in a particular geographic area, and may be configured to respond to data requests from users the same or related geographic areas. For example, a first caching server 120 could be provided in North Carolina to respond to requests based in the eastern United States, a second caching server 120 could be provided in Texas to respond to requests based in the central United States, and a third caching server 120 could be provided in California to respond to requests based in the central United States. In embodiments, two or more caching servers 120 may be operably connected to a single primary server 110. In other embodiments, two or more caching servers 120 may be operably connected to two or more primary servers 110. In embodiments, a system provided herein may contain more caching servers 120 than primary servers 110, more primary servers 110 than caching servers 120, or equal numbers of primary servers 110 and caching servers 120.

Optionally, the network 130 may be any structure which can support the operable connection of and data transfer between two or more computing devices, such as a local area network (LAN) or a wide area network (WAN), and may include, for example, an intranet, an enterprise private network, the Internet, cellular, or satellite networks. The network may include, for example, one or more of wireless connections, wired connections, or fiber optic connections. Computing devices (e.g. servers, external data sources, and user devices) may connect to the network 130 by wired or wireless technologies. For example, a computing device may connect to the network 130 via wired technologies such as a dial-up connection with a modem, a direct link such as TI, ISDN, cable, Firewire, USB, or Ethernet wire. In other examples, a computing device may connect to the network 130 via wireless technologies such as Bluetooth, RTM, infrared (IR), radio frequency (RF), ZigBee, Z-wave, wireless USB, code division multiple access (CDMA) or global system for mobile communications (GSM). In embodiments, data may be encrypted before it is transmitted over the network 130.

Optionally, the external data source 140 may be any computing device which may store, transmit, receive, or gather data that may be accessed by or sent to a server of the system. External data sources include, for example, other servers, hard drives (e.g. IDE, ATA, or SATA drives), databases, personal computers, data storage units, hard drives, portable digital media, smartphones (e.g. Apple iPhone, Android-enabled phone), mobile devices, and computer systems, global positioning system (GPS) devices. An external data source may be portable or non-portable/at a fixed location. In embodiments, an external data source 140 may be capable of obtaining geolocation data, such as by wireless triangulation or a GPS system. In embodiments, an external data source 140 may be on or associated with a subject (e.g. on a subject's wrist or in a subject's pocket or handbag). The external data source 140 may be a portable computing device in proximity to the subject such that the measured location of the device corresponds to the location of the subject. The device may be a portable computing device the subject carries for other purposes. For example, the device may be a smart phone, such as an iPhone or Android-enabled phone, capable of gathering geolocation data, such as with the aid of a GPS module of the device. The device may be an iPad or other portable computing device, such as a watch capable of gathering geolocation data. A client-server relationship, peer-to-peer, or a distributed relationship, may be provided between the external data source 140 and a server of the system. In embodiments, an external data source 140 may communicate directly or indirectly with a server. For example, an external data source 140 may have a direct wired linkage to a server. In another example, an external data source may communicate wirelessly with a server. In another example, an external data source 140 may communicate with a server when the external data source is connected to a personal computer via a wire, and when the personal computer is connected to the Internet. In embodiments, the external data source 140 is operatively coupled to the primary server 110. The external data source 140 may be coupled to the primary server 110 such that data travelling between the external data source 140 and the primary server 110 passes through the caching server 120 as it travels between the external data source 140 and the primary server 110. Alternatively, the external data source 140 may be coupled to the primary server 110 such that data travelling between the external data source 140 and the primary server 110 does not pass through the caching server 120 as it travels between the external data source 140 and the primary server 110. In embodiments, the system may be configured such that the external data source 140 is operatively coupled to the primary server 110 without passing through or involving the caching server 120. With systems and methods provided herein, 1, 2, 3, 4, 5, 10, 15, 20, 25, 100, 1000 or more external data sources 140 may be in communication with a server.

Optionally, the user device 150 may be any computing device with which a user may review, input, request, or change laboratory-test related information. User devices may include, for example, personal computers, tablet computers, smartphones (e.g. Apple iPhone, Android-enabled phone), mobile devices, or computer systems. A user device may be portable or non-portable/at a fixed location. A user device 150 may contain one or more user interfaces. User interfaces may provide information to a user, obtain inputs from a user, or both. A user interface may have a display, such as a cathode ray tube, plasma, liquid crystal display (LCD), or light-emitting diode (LED)—based display. In embodiments, a user interface may include a graphical user interface (GUI) configured to display information to a user on a display, such as appointment time and availability information. A GUI may also be configured to receive information from a user, such as by capacitive or resistive touch-screen functions. In some situations, user interfaces may include camera for video or still images, a microphone for capturing audible information (e.g., a subject's voice), speakers for providing audible information, a printer for printing information, or a projector for displaying images and/or video on a predetermined viewing surface. Other user interfaces of a user device 150 may include, for example, a keyboard, touch pad, or a computer mouse. A user device may contain a processor and local memory and data storage.

In at least some embodiments, certain computing devices may function as both an external data source 140 and a user device 150 for systems provided herein. For example, a GPS receiver-containing tablet computer may both: i) obtain patient location data which is provided to a server running a software program described herein (and thus, function as an external data source 140), and ii) provide a user interface such as a touch screen which may display and receive user input regarding appointment times (and thus, function as a user device 150). In other embodiments, certain computing devices function as either an external data source 140 or a user device 150. For example, a stand-alone hard drive operatively coupled to a primary server 110 is an external data source 140 but not a user device 150. In another example, a computer having a display at a health service center to display appointment time information for patients may function as a user device 150 but not an external data source 140.

In at least some embodiments, a user may be able to interact with software on a server through a client application running on a user device 150. A client application may be, for example, a World Wide Web (WWW)-based interface. A WWW-based interface may be provided, for example, at a specific URL (e.g. a web page), which users may access via the network 130 through a user device 150. A user may request a WWW-based interface at a specific URL, and the content may be delivered to the user device from the primary server 110 or caching server 120. In embodiments, users may input information on a WWW-based interface, and the information may be provided to one or both of the primary server 110 or caching server 120. In embodiments, a WWW-based interface may permit a user to log in to a user account, to permit the user to access one or more interconnected web pages (e.g. web pages associated with the user account). In embodiments, a WWW-based interface may provide laboratory test—related information. With the WWW-based interface, a user may optionally be able to, for example, view appointment-related information, request an appointment, change an appointment date/time, cancel an appointment, or provide special instructions or comments relating to a past or upcoming appointment.

In addition to the system components and configurations described above and elsewhere herein, it is also noted that other suitable system components and configurations may be used with systems and methods provided herein. For example, embodiments of methods provided herein can be implemented in a computing system that includes a back-end component (e.g. a primary server) and a front-end component (e.g. a user computer having a GUI or Web browser through which a user can interact with a computer software for performing methods provided herein), in which the back-end component and front-end component are interconnected by any combination of hardware and software for digital data communication. In other examples, embodiments of methods provided herein can be implemented using a single computing device (e.g. where the computing device stores relevant data, contains one or more processors for performing operations described herein, receives user information, and displays information to a user). Also, it is noted that the relationship between objects depicted in FIG. 2 and elsewhere here is exemplary, and other relationships are within the scope of systems and methods provided herein. For example, although FIG. 2 depicts an external data source 140 being connected to a primary server 110 via a network 130, in embodiments, an external data source may 140 may directly link to a primary server 110 (i.e. without connecting through a network 130).

In at least some embodiments, a home-based CLIA certified testing is provided with the device. In one embodiment, this is a home based analytical device. The system can be a hub configuration wherein a plurality of test and/or collection sites in the field. Some embodiments may be collection sites that then send the sample to central hub portion for processing. Optionally, at least some portion may have remote analyzers at the collection site, wherein the information from the sample is processed at the collection site and then the information delivered to a hub. There may optionally be a telemedicine component wherein the subject at the collection site can consult with a medical professional while still being remote from the "hub". This may optionally provide teal time triage at time a subject is infected, having a rash, showing symptoms, or the like. Some embodiments may use a finger stick, palm stick, ear stick, upper forearm, outer forearm, inner forearm, and/or other target site for a "stick" or tissue penetration(s) to obtain the bodily fluid sample. This can occur at a point of service location. Optionally, teal time results may be obtained wherein the subject can assist or be assisted in the next step of treatment prior to going to a physician's office/facility, prior to going to a pharmacy, and/or prior to leaving a pharmacy (wherein a subject can reduce cycle time by having the correct medication given without having to make separate trip(s) back to the pharmacy to drop off the correct prescription and/or get the correct medication. Optionally, the site can be configured so that a phlebotomist is not required to be present in order to obtain the bodily fluid sample.

In at least some embodiments, eligibility software can be on the analyzer device and/or on website wherein the information about the subject and/or subject's coverage can be confirmed before analyte testing is begun and cartridge and/or reagents are opened and/or used. The insurance eligibility software can optionally connect to a main server and/or caching server that contains the coverage information.

In at least some embodiments, log-journaling is provided wherein there is system recovery for POS medical devices—recover completely from failure like power loss or other fault.

In at least some embodiments, physiological modeling for decision support system (DSS) in an EMR is provided.

In at least some embodiments, real-time feed of CLIA certified lab data into the EMR can be provided.

In at least some embodiments, real-time feed of lab FAA into EMR is provided.

In at least some embodiments, real-time lab data into physiological model is provided.

In at least some embodiments, real-time point-of-service CLIA certified data into EMR for real-time decision making.

In at least some embodiments, real-time point-of-service CLIA certified data into EMR for real-time decision making+CLIA certification.

In at least some embodiments, it should be understood that a social graph is unique. EMR system uniquely ID based on social graph of the user.

In at least some embodiments, telemedicine is integrated with bodily fluid analyzer, wherein doctors get data including but not limited to: 1. Time 2. Space (i.e. Palo Alto) 3. Services (lab, telemedicine, vaccinations, check-up)

In at least some embodiments, three-dimensional (3D) image connection to doctor on VoIP can enable improved telemedicine.

In at least some embodiments, 3D imaging for analysis of target tissue can provide improved telemedicine diagnosis as this provides for additional information for the remotely located medical professional. Optionally, the analytical information about the bodily fluid sample(s) can be combined with the 3D imaging for improved diagnosis procedures.

In at least some embodiments, access .me domain or other web domain database for personal medial information may involve one or more of the following: the system may require ID of device and keep it with data—only that unique device is allowed to access info even if someone has entered the right Id and password to access the account.

In at least some embodiments, accurate care by insurance company can be achieved through automated processes.

In at least some embodiments, the system is configured wherein a user can add a pharmacist—never looking up a collection location, chain, grocery store in local city, or other specifics. Instead, the subject is single-click connected. In such a configuration, a doctor can talk to pharmacists anytime to have true collaboration. This gateway through single-click connection or other techniques can improve treatment. In at least one embodiment, history is recorded in EMR—transcribed. In this non-limiting example, the conversation between x doc and y pharmacist can be included in the EMR. In some embodiments, it can be a transcript, the actual voice and/or video recording, or the like. This can all be part of log; a user can do search. This provides a history of who said what, why medication changed. Optionally, the data from analyte testing, 2D imagery, 3D imagery, and/or the like can also be associated with the EMR conversation documentation.

In at least some embodiments, also for pharmacy—self-check-in method is provided for protecting privacy. Optionally, this can be by way of mobile phone device, mobile computing device, computer kiosk, touch screen monitor, NFC, RFID, and/or the like. Other check-in technologies currently available or those developed in the future are not excluded from use in the self-check-in process. Optionally, the check-in can provide also the information about the user in addition to ID. It can include current medication, last visit, current biometrics, health condition, type of laboratory test requested, etc. . . . so that the system can accelerate the appointment or reduce wait time for certain urgent patients or those with time sensitive and/or fasting type analyte or other testing.

In at least some embodiments, flu testing in retail, including automated and integrated sample prep; flu testing and prescription technology and methodology are combined at retail so that a user can be influenza and/or upper respiratory flu diagnosed at one appointment and medication issued for the detected flu while at or within minutes after the appointment.

In at least some embodiments, anonymous patient imaging of lab order to protect confidentiality; tech interactions; this may optionally include telemedicine—anonymous advice wherein the telemedicine occurs on an anonymous basis, where the doctor does not have subject identification. Some embodiments can also mask, blur, or otherwise protect the identity of one or both of the subject and/or the medical professional so that they are not shown identifying features of each other. Optionally, one or both may appear as animations that mimic the facial and/or body motion so that there is an image, just an animated or cartoon version of the person on the other end of the video.

In at least some embodiments, assays can use low sample volume chemistry—irrespective of device. In at least one embodiment, there is low volume of sample because of no tubing between starting vessel and destination vessel in the device in which sample must be flowed or passed in order to conduct analysis.

In at least some embodiments, automated 24 hour urine device for use in patient service centers allows for a subject to collect at home or other convenient location and then drop off at service centers in retails or other locations that maintain hours of operations longer than those of a medical professionals clinic hours.

In at least some embodiments, biometric data web ID—fingerprint or external or analyte signature can be used as ID and/or as identification of the sample. In this manner, the sample can be double verified based on the ID initially presented and ID further verified based on genetic or biological information that has be confirmed in previous testing and/or from other databases. PCT/US2013/058450 is fully incorporated herein by reference for all purposes regarding the use of genetic signature, which can be part of the at least double ID verification. Optionally, some embodiments do not even require initial user ID verification. A user can simply state their identification (without third party or other verification) and ID will be established based on the ID generated from the sample testing. Optionally, this provides built in fraud abuse and misappropriation of services and testing for labs (or prescriptions or secondary procedures like scans) based on history and lab data.

In at least some embodiments, a call center CRM app can be used on a mobile computing device and/or desktop or other computer to connect medical professionals and patients to arrange for and/or discuss laboratory testing. In at least some jurisdictions, a subject is directed to obtain a prescription before laboratory testing order can be fully confirmed and initiated.

In at least some embodiments, a system is provided to capture screen shot—context aware screen scraping can be used. This clipping of information can be used to capture information about the subject, the laboratory order, the test results, subject condition, subject history, and/or other information.

In at least some embodiments, a subject can check-in online and/or have online reservation; tech app suite. This check-in for lab can provide for more advanced and efficient queuing at the patient service center site.

In at least some embodiments, test results are given to lab and communicated from the lab (via cloud) to the desired recipient(s). By way of non-limiting example, the desired recipient may be a user, the user's medical professional, the insurance company or the like. Optionally, the recipient list can be limited based on patient privacy and/or other compliance regulations and laws.

In at least some embodiments, a CLIA lab in box is provided that uses a sub-1 mL sample to provide at plurality of analyte levels. In one embodiment, a single housing for a portable device is provided wherein a plurality of assays can be run that are of CLIA-compliance.

In at least some embodiments, a CLIA lab is in located an airport and/or other transportation terminal. In one non-limiting example, this lab is capable of using a sub 1 mL sample to provide at plurality of analyte levels. This can be of particular use as often subjects can have extensive wait times wherein issues can be addressed using time that would otherwise be wasted and the small sample volume can also simplify and/or expedite the collection process. Advanced check-in can allow for a user be in a virtual queue while waiting for their turn. Optionally, some may have a special entrance as the analyte/genetic testing can be used to verify the subject ID and a user can bypass the usual security lines if entering through the laboratory entrance to the transport facility and that the testing includes ID verification through analytes and/or other ID.

In at least some embodiments, a CLIA-waived sample processing unit (SPU) is used that sends data to a Theranos virtual analyzer (TVA). In one embodiment, the TVA is an analyzer that takes electronic or digital information about a sample and processes that information to obtain analytical information about the sample and/or analytes therein. One non-limiting example of a TVA and this data can be found in U.S. patent application Ser. No. 61/766,095 filed Feb. 18, 2013 and fully incorporated herein by reference for all purposes.

In at least some embodiments, some embodiments may have CLIA waiver and certification simultaneously. Optionally, some portions may be waived while other portions are certified.

In at least some embodiments, system(s) herein may use one or more CLIA—waivable point-of-service devices that has on-board controls and wherein the sample processing unit or other hardware is calibrated on the consumable. Optionally, the point-of-service devices can operate at the patient service center, a retailer with such a sample collection location, or the like that is physically remote from a central laboratory. In one non-limiting example, the device has on-board controls and calibrators substantially equivalent to those devices that are in a CLIA compliant laboratory, except that the device is short of having the paperwork deeming it in CLIA compliance.

In at least some embodiments, the system may include cluster management—cartridges, robots, machines, and other equipment that send events to it. Optionally, the system may include a smart queuing system that coordinates machine availability, optimizes run time, speed/moving distance, run the sample processing units, and/or multiplexing. Optionally, some embodiments may provide automated instructions to the system regarding one or more of the features described herein.

In at least some embodiments, compliance with sample collection and/or patient testing is increased. Optionally, web and/or GPS based sensing for medical device monitoring can allow for improved compliance. Optionally, the system can provide a cart assembly on demand and dispatch it to the desired room and/or location.

In at least some embodiments, data network connectivity is provided with the device. Optionally, the connectivity is a form of lab link between patients, doctors, and/or labs. Optionally, the device can automatically transmit what sample or tissue is being looking at.

In at least some embodiments, coupons can be entered by the user to cover and/or reduce testing cost. The coupons may be codes, barcodes, or other format. This can be entered online, through a mobile device, or physically at the service site.

In at least some embodiments, payment and/or coupons can cover tests both non waived and waived.

In at least some embodiments, "credit" score(s) for health based on baseline can be provided. Optionally, this score can be a calculated value based on a multiple variables about a user's health, wellness, and/or health lifestyle. Optionally, this can be used for jobs and insurance and reimbursements from both. Optionally, this score can include a plurality of analyte measurements, trending of analyte levels, velocity of change of analyte levels, and/or other health indicators. Optionally, certain variables can be weighted more heavily to increase their impact on the score. Optionally, certain variables can be weighed less heavily to decrease their impact on the score. Optionally, some embodiments can have a non-weighted system for score calculation. Optionally, the score can be used to inform a subject of which variable is having significant impact on their score and/or to encourage a subject to change that variable, such as but not limited to showing the change in their score based on certain changes in the variable(s). Optionally, based on when a score was last updated, a reminder can be emailed, mailed, texted, SMS'd, or otherwise notified to encourage them to submit samples or otherwise update their score information. Optionally, anonymized information about trends of scores of other individuals in a similar geographic area and/or those with similar backgrounds can also be sent to the user to compare their score to those in the area.

In at least some embodiments, a dashboard and/or high level summary-type user interface is provided on a webpage, software, and/or other information display for the subject. In one non-limiting example, to the extent allowable under law and/or regulations, employers can manage dashboard of patients. Optionally, anonymous health EMR of employee base can be created using the information. Optionally, some embodiments may provide a company health portal that can be a website or server that is accessible by the internet or by a native device application such as a mobile phone application or the like. In this non-limiting example, a company's patients are encouraged to go to pharmacy and lab that are in the company's network. Optionally, some embodiments may allow for samples to be obtained at locations such as but not limited to retail locations and/or other distributed locations. Optionally, the system can be used for health screenings that can function as surveillance baseline for employers. Optionally, health progress can be shown quarterly for employers. Although the embodiments herein are described in the context of employers, it should be understood that these embodiments can be adapted for use with other groupings of individuals not based on employment, such as but not limited to school-based groupings, insurance provider groupings, geographic (city, county, state, etc. . . . ) grouping, and/or other groupings.

In at least some embodiments, data to or from the sample processing unit can be saved on flash memory, SD card, microSD card, flash memory, memory unit with a USB or other interface, and/or other portable memory unit. The physical memory storage unit can be shipped, driven, or otherwise delivered to another facility for "sample" analysis. This can be particularly desirable in areas where data connectivity may be sporadic or where the system desires to provide greater data security through the use of physical transport of data that cannot be electronically intercepted.

In at least some embodiments, the analytical results from the sample analysis can be used in decision making. In one non-limiting example, decision support is used in the form of analytical software that incorporates analyte measurement(s) along with other patient information and/or other peripheral information to assist in decision support.

In at least some embodiments, device control comprises central control of all devices from the cloud (in a CLIA-compliant manner), including but not limited to systems upgrades and controls and all application level controls, as well as hardware controls (mechanics, robotics) and oversight.

In at least some embodiments, a system is provided for displaying test results. In one embodiment, the system displays results right there on the analyzer. In one embodiment, the system displays results right there on the sample processing units. In one embodiment, the system displays results on a portable display unit that may be part of mobile phone, smart phone, and/or mobile computing device. Optionally, the results can be those based on data transmitted to analytical site that then reports back to the sample processing unit the test results. Optionally, some embodiments can process samples and analyze samples using devices at locations remote from a central laboratory.

In at least some embodiments, disposables such as but not limited to pipette tips, assays units, reagent vessels, or similar components are located off-board a sample processing unit. In one non-limiting example, the off-board location is only in regards to when the disposables are not in use with the sample processing unit.

In at least some embodiments, doctors also leverage telemedicine infrastructure—wherein such telemedicine feature is to be available on patient's time.

In at least some embodiments, dynamic scheduling appointment system is provided wherein one non-limiting example provides for looking at real-time traffic in patient service center locations (people in line/queue, etc. . . . ); one embodiment may use other sensors such as smart phones—someone walking toward our lab/healthcare service location know on way. This may all feeds into a scheduling system. Some embodiments may look at how long it is taking to process each patient on average and this information may be stored in a database for other uses. In one non-limiting example, appointment windows adjust dynamically—fully adynamic based on patient flow, queue, implicit intent (i.e. patient walking toward a grocery store with the patient service center, even though they didn't check in we know based on geo-location/sensors they're coming), performance of technicians in space, people helping check in—all data feeds into system. In one non-limiting example, the appointment window adjust is based on at least two of the foregoing factor. Based on that give patients window that is very accurate when show up. In one embodiment, the system provide a time window not a static time. When arrive, put patient in queue. If come first, processed first, come last within window still guaranteed a spot.

In at least some embodiments, early check-in may be available for users to check-in to their appointment before they actually reach the physical location of the sample collection facility.

In at least some embodiments, some embodiments may use an electronic game based on user health information.

In at least some embodiments, a sample processing unit may be physically located on, embedded, or otherwise operating in a vehicle—plane, boat, space, ship, ambulance, car, tank, or other mobile platform(s). Optionally, a CLIA-compliant or other regulatory compliant sample analyzer may be physically located on, embedded, or otherwise operating in a vehicle—plane, boat, space, ship, ambulance, car, tank, or other mobile platform(s).

In at least some embodiments, emergency transit testing may be performed on a subject to increase survival rate. Thus, where a sample processing unit is on the vehicle transporting the subject, the sample from the subject can be processed to obtain subject data that may be used to determine a desired course of treatment.

In at least some embodiments, EMR can be accessed using .md website domain. Optionally, EMR and apps can be used wherein physicians and or other authorized professionals are paid for meaningful use and transactions using at least some embodiments of this system, wherein automatically through insurance or other reimbursement.

In at least some embodiments, an EMR is provided that is designed for retail care and urgent care: diet, grocery data, pharmacy data, lab, radiology—using image analysis/remote radiologist for interpretation (radiologist not needed on staff in urgent care), symptoms, history (comprehensive) embedded across all retail sites from all datapoints collected and analyzed in real-time; webex standard or other teleconference capability embedded into EMR (built in)—physicians can do telemedicine or share sessions and screens with other doctors, specialists, clinicians for a given session (only) to get second opinions live; scheduling of staff, monitoring hours, audit trails, controlled log-in In at least some embodiments, a system is provided that comprises an EMR lab exchange. In one non-limiting example, lab-based EMR may comprise but is not limited to—notes and CRM integrated for lab conversations, pathologist analyses, everything as if lab is their lab in house. Some embodiments may comprise a tool bar in EMR for chat, email, phone, video—click and lab director always there for them. Some embodiments may comprise a chat feature with "your agent"—nurse, lab director—see status—in EMR show available, free (lync or other system) like chats online—see busy, chats.

In at least some embodiments, one can enter data into system creating data out of it.

In at least some embodiments, for example diagnosis (dx) of epiglottis versus pneumonia infection—the desire is to properly diagnose and treat actual disease not symptoms disease. In one non-limiting example, the diagnosis (dx) may be based on multiple variables and/or measurements to provide more data for diagnosis.

In at least some embodiments, a customer relationship management (CRM) system is provided with physicians and patients. In one non-limiting example, a CRM is configured for managing interactions with current and future customers. It often involves using technology to organize, automate and synchronize various functions such as but not limited to sales, marketing, customer service, and technical support. In one embodiment, the physicians may be in communication with patient(s). Optionally, the parties are in communications with an entity that handles testing services.

In at least some embodiments, a food diary is provided that may be a food portion sizine.

In at least some embodiments, fresh sample is available for use with the sample processing unit. In one non-limiting example, no decay rate is associated with the sample as the sample is processed for analyte measurements at the collection site. Pre-analytic processing can also occur on samples at the collection site soon after collection. This may be beneficial if the sample will be processed at a later point in time and not immediately after collection.

In at least some embodiments, social media or peer-to-peer information may be provided for a variety of reasons including but not limited to compliance. For example, one embodiment may use friends lab data for comparatives such as but not limited to—who is unhealthiest in cluster—who has worst negative influence (i.e. cholesterol levels of friends and their friends) or other categories. As habits can be contagious, good ones can be used to influence others to take healthier action(s). Algorithm can be used for displaying a health graph and/or health influencers. House cleanliness based on diet. Flower growth based on diet. Do something about a user's health and garden flourishes. It should be understood that other motivational type games such as keeping an electronic pet alive by doing tasks related to your health can also be one way to keep feed or otherwise keep the electronic pet alive.

In at least some embodiments, finger stick (FS) based chemistry @ retail on genetic tests. This can be applicable to bodily fluid sample acquired from fingerstick on capillary blood. It may also be available on small volumes (1 mL or less) of venous blood.

In at least some embodiments, fingerstick CLIA lab testing is provided in one non-limiting example, by using live blood fingerstick transport, wherein the blood sample is not dried down.

In at least some embodiments, fully transparent testing and test reporting—testing for xyz markers—score is component of abc, wherein testing and results are clearly noted.

In at least some embodiments, the workflow for testing procedure may involve at least one or more of the following: get credit card info entered; get coupon number/give it to tech when check-in through iPhone or other smart phone/scan it—confirm paid for—for anonymous pay from own pocket—don't even need Id—truly anonymous direct-to-consumer test. Optionally, some embodiments may involve two or more of the foregoing. Optionally, some embodiments may involve three or more of the foregoing.

In at least some embodiments, data from a laboratory test goes to EMR. This may occur simultaneously with a report being sent to a medical professional such as but not limited to a doctor. Optionally, the sending to the EMR may occur before or after notification to the medical professional.

In at least some embodiments, the sample processing unit(s) may be deployed at a grocery store and/or pharmacist accountable care organization.

In at least some embodiments, heating pad(s) may be used to prepare a target site on a subject for sample collection.

In at least some embodiments, some systems may have an image capture, data capture, or other system where one can hold a sample container such as but not limited to a Nanotainer vessel up to computer screen with a web cam or other data capture device to image the barcode or data capture the barcode on such container.

In at least some embodiments, hospital telepathology may be used to review sample located at a site remote from the hospital pathologist.

In at least some embodiments, image analysis algorithms may be used for histology images. In one non-limiting example, the image analysis algorithm can be used to more methodically analyze an area of interest in the image.

In at least some embodiments, some systems may use image analysis on screen for EMRs—wherein this may involve scanning whole EMR screen.

In at least some embodiments, the reports or results may include images to docs in report and pathologists in test review and diagnosis. Such images may provide additional information that may change the way doctors diagnose (wherein such images may show how cells move, cell features, etc. . . . ). Include images of bugs. Images of everything everywhere.

In at least some embodiments, the system may comprise of a mobile computing system, wherein in app will ask for unique private certificate only for a given user—only public private cert that can encrypt data—use to decrypt—have to have cert to do so. In this non-limiting example, this provides an enhanced level of security for user information.

In at least some embodiments, the system may include analyte testing for pets and other animals. The system may be adapted for use to a vertebrate, such as a mammal to include, but are not limited to, murines, simians, humans, farm animals, sport animals, and pets.

In at least some embodiments, individual clinical decision support (CDS)—your patients and practice.

In at least some embodiments, integrated sample preparation is part of a sample processing unit. In at least some embodiments, integrated sample preparation is part of a sample analyzer. In this manner, errors and variation associated with manual sample preparation is reduced.

In at least some embodiments, the test results are reported in a format that includes integration of histology images (whole tissues) with rest of laboratory data. Optionally, in addition to still images, some may include video or motion-based images. The format may be for written media, electronic media, audio media, tactile media and/or other forms of reporting information.

In at least some embodiments, Intelimet—intelligent estimate of $; Intelisense Intellidraw; Intelligent eligibility—which tests Interactive.

In at least some embodiments, what is provided herein is an inversion of central lab model, not having to wait for 96 samples or some other batch number of samples to be ready before samples are processed for analyte measurements; instead a sample is run when it is ready, even if it is only a single sample.

In at least some embodiments, Laboratory service model; Las; Lbm

In at least some embodiments, LDT regulatory model

In at least some embodiments, LPr laryngopharyngeal reflux (LPR),

In at least some embodiments, marketing—security may be part of the sample transport processing, and this may include but is not limited to badging around sample custody—couriers badging in and out of patient service center app.

In at least some embodiments, mobile phone job search—like a profile—match to job descriptions based on sets of ~20 skill sets In at least some embodiments, Monitor for drug efficacy and safety at pharmacy In at least some embodiments, data needs key for decryption.

In at least some embodiments, new standard of care for URLR—strains, ELISAs, CBC, chem14 @ POS retail <20 mins In at least some embodiments, the process for analyte measurement(s) may involve using one lab that is waived, other certified, and exchanging data to complete a test. In another embodiment, only the certified laboratory will report the completed test result.

In at least some embodiments, a Vitamin D assay is provided wherein the speed and sample volume of the assay and portability of the assay solution allow for the assay to be run @ retail.

In at least some embodiments, the method uses a system for laboratory test request wherein the ordering—form involves optical character recognition (OCR) and automatic reading and transmission (back to lab) and processing.

In at least some embodiments, the system comprises an EMR with images of lab data. In one embodiment, the EMR has images not only of analyte results, but additional images such as but not limited to cells, tissue, or other bodily sample not traditionally found in typical laboratory reports. In this manner, additional data is provided to the healthcare provider or medical profession to assist in decision making. In one embodiment, an EMR based on lab is provided.

In at least some embodiments, payors mandate retail deployment of the system. Send payors data. Payor nurses provide care. Send them the data; while in pharmacy, prescription(s) is provided. No need for separate office visit for separate prescription.

In at least some embodiments, PHARMA and drug interface information (in EMR) to lab results and patient data for info on efficacy and safety/potential impact projected.

In at least some embodiments, PHARMA dss, telemedicine, asynchronous connections to expert Md/pharmaco. Train techs and pharmacists on drugs.

In at least some embodiments, pharmacy data and lab data are integrated for most meaningful clinical information and DSS; predictive analysis is provided based on the laboratory data and patient data in the EMR.

In at least some embodiments, the system comprises pharmacy dispensing sourcing at any location is provided.

In at least some embodiments, physician automatically checks patient in through software.

In at least some embodiments, physician rely for clinical decision making.

In at least some embodiments, physicians and patients simultaneously in a CRM-type software.

In at least some embodiments, point of care device as clinical analyzer under 862.xx is provided herein. In one embodiment, the system comprises clinical chemistry and/or clinical toxicology devices that can perform at least two or more tests listed in CFR Title 21, Chapter I, Subchpater H, Part 862.

In at least some embodiments, process management system is provided.

In at least some embodiments, PSC as a service is provided, wherein the PSC operates to provide a service and a portion of fees is paid to the owner of the physical site where the PSC is operating. In at least some embodiments, the system comprises a reimbursement for services.

In at least some embodiments, pull patient info.

In at least some embodiments, raw results or data from a sample processing unit may either be handed to local T-virtual-analyzer (TVA) and/or if find it for processing, then cloud TVA. Optionally, the system may be configured to always have two checkpoints. All done by rms.

In at least some embodiments, reporting—compliance is provided by the system in regards to patient testing and/or compliance with medication take (based at least in part on analyte measurements which may or may not show enough of the drug or changes in analyte measurements that are associated with the drug. Pharmacokinetic and/or pharmacodynamic information is used to measuring compliance.)

In at least some embodiments, results available right away for docs, based on electronic delivery directly to docs or based on input of the results in an EMR or LIS and providing a notification to the doctor.

In at least some embodiments, retail clinic devices are provided for sample processing. Optionally, some may include a virtual analyzer for test analysis.

In at least some embodiments, Retail pharmacy or other consumer frequented sites may be used to implement a retail PSC. This may allow sample collection and/or shipment.

In at least some embodiments, realtime transfusions may be facilitated by realtime donor blood and/or recipient blood analysis. In this manner, delays associated with traditional blood transfusion is minimized. It may also introduce an on-demand model wherein blood is more directly transferred to a recipient due in part for the reduced amount of time to obtain information about donor blood and/or recipient blood.

In at least some embodiments, tertiary information about the user can be used to sort information and/or to motivate a subject for improved health outcomes. By way of non-limiting example, some embodiments may see if the users are runners, broccoli eaters or other category. This may be used to have influence on Friends. Optionally, the system may also state what change people—i.e. have child, their family, or friends health get worse. Change in state or geography. Lifestyles. These can all be included as factors in the overall health analysis.

In at least some embodiments, saliva sample is collected from the subject while they are at a retail location.

In at least some embodiments, same certificate moved to new devices as needed (only one device at time private cert). This can provide for an enhanced level of security.

In at least some embodiments, one can scan insurance card on portable device in check-in app (mobile, tablet, wearable device, or other device) for labs and healthcare service.

In at least some embodiments, a method of processing comprises scanning patient sample tubes @ physicians office—automatically linked to patient. In such an embodiment, the tubes may be microsample tubes wherein the tubes already include barcodes on them and the process then associates the barcode (or a tube specific identifier) with the subject, instead of a traditional mode that associates subject ID with an originally unmarked tube. This embodiment inverts the traditional model of having the subject ID added to the collection vessel, which is different from having a collection vessel ID associated with a subject.

In at least some embodiments, a score is associated with images from a subject's laboratory test. In one embodiment, the image may be an image of a blood cell from the subject's sample. The system may then give coupons (physical or electronic) to get tested (free, discounted, or other incentive) if the subject does not have score on social network.

In at least some embodiments, the system may be used to search patient for various markers.

In at least some embodiments, security screenings can be based on analyte measurements for a select group of markers.

In at least some embodiments, the system may have a method to see neighbor health/who is dying in virtual world as a representation of the neighbor's health.

In at least some embodiments, signal travelling between sample processing device to CLIA lab—can be through USB key or other physical data storage medium instead of through an entirely electronic transmission. In this manner of a physical transport of a medium containing electronic data may be implemented.

In at least some embodiments, the system comprises a single touch blood drop onto system directly and integrated sample prep in the sample process unit.

In at least some embodiments, SIPS smarter—exposes more and more services. See and make sure module done, for example.

In at least some embodiments, Skype, FaceTime, or other video call integration may be included in the sample processing unit or an interface in communication therewith so that video and/or still image information can also be provided along with any other sample or analyte information.

In at least some embodiments, the system may be used for sports testing to detect for performance enhancing drugs or other banned substances.

In at least some embodiments, the system is configured to provide analyte measurement results at retail or POS in <1 hr.

In at least some embodiments, the system comprises at least a table with finger warmer and/or barcode scanner in PSC.

In at least some embodiments, the method provided herein comprises telemedicine with integrated labs (through the sample processing unit, integrated video conferencing).

In at least some embodiments, the method provided herein uses telemedicine with Payor's nurse.

In at least some embodiments, the system may provide testing of the operator wherein the system uses quizzes, certs, check-in mapping, when looked at SOP and how long, etc. . . . for testing purposes and oversight.

In at least some embodiments, testing of bodily samples may occur at airport as part of a convenience for travelers who may be on lay-over from connecting flights. Such a system may include having a PSC in the airport wherein samples are processed and not sent outside of the secured area of the airport. Optionally, some embodiments may also use analyte measurements for airport security screening purposes, wherein such collection may be used as part of the security screening. Optionally, this analyte testing may occur only for passengers selected for secondary or heightened screening and not every passenger or subject going through initial screening will be tested.

In at least some embodiments, at least a part of the process may be implemented through mobile phone.

In at least some embodiments, TPS.

In at least some embodiments, transmits data to external device (such as but not limited to the cloud)

In at least some embodiments, a virtual analyzer is in a CLIA certified lab (LAS) and not at the sample collection and/or processing location.

In at least some embodiments, the system may use public key for encrypt—even Theranos or the company or entity operating laboratory cannot see (except for regulatory purposes)—highly sensitive tests.

In at least some embodiments, user can request analyte testing.

In at least some embodiments, a variance in lab error is repeated in EMR. Some embodiments may detect this variance and repeat testing or processing on the sample.

In at least some embodiments, the system may send a video to patient and bill.

In at least some embodiments, VIP patient may have expedited processing or queuing. Some embodiments may have a VIP status designated based on urgency of testing or where the user (for additional cost or other consideration) requested heightened processing.

In at least some embodiments, the system may comprise using a waived device (SPU) and certified tests.

In at least some embodiments, the system may comprise using waived devices and CLIA lab oversight (location of the devices still psc and waived).

In at least some embodiments, the system may comprise using waived SPU that sends data to certified lab or LAS in certified lab.

In at least some embodiments, the laboratory does billing, retail etc. (like itunes) and the entity owning the retail facility where the PSC is located does not handing the billing.

In at least some embodiments, the system uses waived device (SPU) and certified tests.

In at least some embodiments, testing herein can have applications on mobile location such as boats, submarines, or other transport vehicles. One can also have application in Pediatric HIV testing.

In at least some embodiments, the system may comprises a website such as but not limited to one with a .MD domain like app store, itunes, with apps that allow for all things including communication and transcripting with ability to rate techs etc; create accountability, both edit. In this manner, a social media and feedback system can be included as part of the overall system.

In at least some embodiments, the system may deploy PSCs in homes, physician's offices (with or without devices), retail—drop down on our apps allows people to choose which lab/hospital they want to oversee their test and be connected with. In this manner, one PSC can collect samples for a number of different labs/hospitals, wherein the information electronically associated with the sample will determine where the analyte information is routed for analysis.

In at least some embodiments, "Bloomberg" terminal for doctors, wherein a doctor may have a designated workstation for obtaining data with a direct feed to the laboratory information system and/or EMR. In one embodiment, this dedicated station may have a custom interface and/or dedicated network connection to facilitate in the dissemination of information to the user. Optionally, the system can provide a terminal or other user device that a user can monitor and analyze real-time patient health and/or laboratory test data and place orders (for labs or action by medical staff) on the electronic platform. In one embodiment, the system also provides news, system status information, and messaging across its proprietary secure network. The system may also use a tablet or other interface and is not tied to only a desktop computer.

In at least some embodiments, context information about the user may be used and get leverage—social, @ work, blood pressure makes angry . . . may not realize unless full picture with contextual information is associated with the test results.

In at least some embodiments, device process any new test (cloud)—influenza based on upload of new protocol (wirelessly or by coupling of physical media to the device for the update).

In at least some embodiments, the system may have an alcohol swab/dispensing machine, wherein such a machine may be attached to the sample processing unit or physically separate but still associated therewith. In one embodiment, the system may be configured for automatic cleanse and dry.

In at least some embodiments, the user does not have to type or take picture to get lab request sent.

In at least some embodiments, decision support system is integrated into EMR around lab results. Front end eligibility—rules—number of tests, just ordered, best practices Back end—fraud and abuse.

In at least some embodiments, dual screen 3d graphics and video conference data terminals may be used to display information to the medical professional or other user.

In at least some embodiments, dynamic standard operation procedures (SOPs) based on where are (location) of the sample processing unit.

In at least some embodiments, proposed testing both the single-sample and six-sample models as the six-sample model is identical to the single-sample model—just literally replicated six times for redundancy.

In at least some embodiments, room completely automated, refrigerated, in hospital (for example), cartridges pre-stored and automatic sample entry and loading. In this manner, the entire storage and sample entry and loading can occur in one environmental enclosure.

In at least some embodiments, sample faster by scanning bracelet of subject to collect their information. This can also be used alone or in conjunction with at least a secondary method of ID verification.

In at least some embodiments, the system may use secure lab lync channel—secure private cloud connection.

In at least some embodiments, the remote analyzer sends heartbeat and/or similar messaging to cloud and/or a remote server so that the uptime and/or availability is noted and/or confirmed in the system.

In at least some embodiments, sensors in vehicles—medevac, ambulance, and cars: safety of driving and linkage to physicians, wherein such information may be captured and conveyed to the appropriate personnel.

In at least some embodiments, the system comprises a voice-activated assistant app, such as but not limited to Siri or similar system, built into the operating system of a computing device that allows users to interact with the device by voice, wherein the device or software is activated based in part on the context (THE vocabulary)—i.e. food—rich in calcium. Smart phone is source of info/education.

In at least some embodiments, ultimately all test are read through blood—siri or other voice-activated assistant app educates the subject on the results.

In at least some embodiments, the system may use ultrasonics and gauge to measure depth.

In at least some embodiments, the system may video doctor interaction—EMR—through devices.

In at least some embodiments, the system may use video in DMS and integrated at PSC level—training and testing and reminders.

In at least some embodiments, voice activated EMR can be used with embodiments herein.

In at least some embodiments, water monitoring applications of the analyzer include but are not limited to dialysis, industrial plants, drinking water treatment plants, and/or Bacteria detection in all of the above.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the user interfaces herein are not limited to IOS or Android and that other operating systems are not excluded.

For some embodiments herein, as data is sent to the cloud, the metadata in the file may be corrupted or not provide desired information regarding when test was taken. Some embodiments herein may opt not to use any of the metadata associated with the data. Optionally, some embodiments may extract metadata at the device and include it as part of the data such as but not limited to a value of one or more the data fields that are transmitted, instead of residing in the background as metadata. Optionally, the harvesting of the metadata can occur in the cloud. It may continue to be part of the metadata of the file or it can be incorporated into one or more the data fields that are transmitted onward to the laboratory.

Some embodiments herein may include an opt-in and/or opt-out user interface page or question so that the user may select the privacy, clinical trial, and/or other participation in programs associated with the user and/or the test data.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are also fully incorporated herein by reference for all purposes: U.S. Pat. App. Ser. No. 61/875,033, filed Sep. 7, 2013: U.S. Pat. App. Ser. No. 61/875,687, filed Sep. 9, 2013, U.S. Application Ser. No. 61/959,958, filed Sep. 6, 2013, U.S. Patent Publication 2005/0100937, U.S. Pat. No. 8,380,541; U.S. Pat. App. Ser. No. 61/766,113, filed Feb. 18, 2013; U.S. patent application Ser. No. 13/769,798, filed Feb. 18, 2013; U.S. patent application Ser. No. 13/769,779, filed Feb. 18, 2013; U.S. patent application Ser. No. 13/769,820, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. A method comprising:
clinical laboratory testing using less than 1 mL of sample from a subject comprising:
inserting a cartridge containing the sample and all reagents into a benchtop sample processing device;
using said sample processing device that has on-board controls and wherein the sample processing device is calibrated on a consumable provided by the cartridge;
using a convective flow unit of the sample processing device to thermally maintain a desired air temperature range within substantially light tight confines of the sample processing device, wherein a filtered outlet is provided to filter air exhausting from the sample processing device; and
processing the sample within the light tight, temperature controlled environment of the sample processing device to measure at least one analyte in the sample.

2. A method comprising:
clinical laboratory testing using less than 1 mL but more than 20µL of sample from a subject comprising:
inserting a cartridge containing the sample and all reagents into a benchtop sample processing device;
using said sample processing device that has on-board controls and wherein the sample processing device is calibrated on a consumable provided by the cartridge;
using a convective flow unit of the sample processing device to thermally maintain a desired air temperature range within substantially light tight confines of the sample processing device, wherein a filtered outlet is provided to filter air exhausting from the sample processing device; and
processing the sample within the light tight, temperature controlled environment of the sample processing device to measure at least one analyte in the sample.

3. A method comprising:
using a mobile computing device to schedule an appointment time for a laboratory test;
displaying a laboratory test menu on the mobile computing device, selecting one or more tests from said test menu, wherein the test menu is variable-based on geographic location; and
using eligibility software to confirm information about a subject and/or subject's coverage before analyte testing is begun and cartridge and/or reagents are opened and/or used;
inserting the cartridge containing the sample and all reagents into a benchtop sample processing device;
using said sample processing device that has on-board controls and wherein the sample processing device is calibrated on a consumable provided by the cartridge;
using a convective flow unit of the sample processing device to thermally maintain a desired air temperature range within substantially light tight confines of the sample processing device, wherein a filtered outlet is provided to filter air exhausting from the sample processing device; and
processing the sample within the light tight, temperature controlled environment of the sample processing device to measure at least one analyte in the sample.

4. The method of claim 1 wherein said clinical laboratory testing is initiated from a consumer ordered laboratory test request.

5. The method of claim 2 wherein said clinical laboratory testing is initiated from a consumer ordered laboratory test request.

6. The method of claim 1 wherein said clinical laboratory testing is initiated from a laboratory test request document scanned by optical character recognition and electronically transmitted to a laboratory where the clinical laboratory testing is to be performed.

7. The method of claim 2 wherein said clinical laboratory testing is initiated from a laboratory test request document scanned by optical character recognition and electronically transmitted to a laboratory where the clinical laboratory testing is to be performed.

8. The method of claim 3 wherein said laboratory test is initiated from a consumer ordered laboratory test request.

9. The method of claim 3 wherein said laboratory test is initiated from a laboratory test request document scanned by optical character recognition and electronically transmitted to a laboratory.

* * * * *